United States Patent
Brearley et al.

(10) Patent No.: US 9,814,918 B2
(45) Date of Patent: Nov. 14, 2017

(54) MICROBIAL DEACTIVATION OF EXPLOSIVE COMPOSITIONS

(71) Applicant: ORICA INTERNATIONAL PTE LTD, Singapore (SG)

(72) Inventors: Clint Brearley, Montmorency (AU); Steven Kotsonis, Brunswick (AU); Kaiyan Liu, Bundoora (AU); Thomas Smylie, Kurri Kurri (AU); Richard Goodridge, Parker, CO (US)

(73) Assignee: ORICA INTERNATIONAL PTE LTD, Singapore (SG)

( * ) Notice: Subject to any disclaimer, the term of this patent is extended or adjusted under 35 U.S.C. 154(b) by 69 days.

(21) Appl. No.: 14/376,339

(22) PCT Filed: Jan. 29, 2013

(86) PCT No.: PCT/AU2013/000072
§ 371 (c)(1),
(2) Date: Aug. 1, 2014

(87) PCT Pub. No.: WO2013/113058
PCT Pub. Date: Aug. 8, 2013

(65) Prior Publication Data
US 2014/0377844 A1 Dec. 25, 2014

(30) Foreign Application Priority Data
Feb. 2, 2012 (AU) ................ 2012900382

(51) Int. Cl.
| | | |
|---|---|---|
| *C02F 3/34* | (2006.01) | |
| *A62D 3/02* | (2007.01) | |
| *C06B 21/00* | (2006.01) | |
| *C12N 1/38* | (2006.01) | |
| *C12N 9/02* | (2006.01) | |
| *C12N 9/04* | (2006.01) | |
| *C12N 9/06* | (2006.01) | |
| *C12N 1/20* | (2006.01) | |
| *A62D 101/06* | (2007.01) | |

(52) U.S. Cl.
CPC ............ *A62D 3/02* (2013.01); *C06B 21/0091* (2013.01); *C12N 1/20* (2013.01); *C12N 1/38* (2013.01); *C12N 9/001* (2013.01); *C12N 9/0004* (2013.01); *C12N 9/0006* (2013.01); *C12N 9/0036* (2013.01); *C12N 9/0044* (2013.01); *A62D 2101/06* (2013.01)

(58) Field of Classification Search
None
See application file for complete search history.

(56) References Cited

U.S. PATENT DOCUMENTS

| | | |
|---|---|---|
| 3,036,939 A | 5/1962 | Clamp |
| 3,359,334 A | 12/1967 | Gold et al. |
| 3,692,682 A | 9/1972 | Glendale et al. |
| 3,872,159 A | 3/1975 | Marcus |
| 4,533,415 A | 8/1985 | Wagner et al. |
| 2014/0352567 A1 | 12/2014 | Cooper et al. |
| 2015/0218061 A1 | 8/2015 | Cooper et al. |
| 2016/0145165 A1 | 5/2016 | Zank et al. |
| 2016/0146587 A1 | 5/2016 | Zank et al. |

FOREIGN PATENT DOCUMENTS

| | | |
|---|---|---|
| WO | WO 97/19253 | 5/1997 |
| WO | WO 98/55822 | 12/1998 |
| WO | WO 99/59742 | 11/1999 |
| WO | WO 2009/026184 | 2/2009 |
| WO | WO 2009/094714 | 8/2009 |
| WO | WO 2009/094716 A1 * | 9/2009 |

OTHER PUBLICATIONS

Colemen et al., Journal of Applied Microbiology, 2002, vol. 93, p. 463-472.*
Snape et al., Journal of Bacteriology, Dec. 1997, vol. 179, No. 25, p. 7796-7802.*
Talalay et al., Proc. Natl. Acad. Sci., Medical Sciences, 1988, vol. 85, p. 8261-8265.*
IUBMB Enzyme nomenclature for EC 1.6.5.2, downloaded from the IUBMB website on Jun. 8, 2016.*
Patent Examination Report No. 1 for Australian Application No. 2013214684, dated Aug. 4, 2015, 2 pages.
Supplementary European Search Report for European Application No. 13744139.0, dated Oct. 7, 2015, 8 pages.
International Search Report and Written Opinion for International Application No. PCT/AU2013/000072, dated Apr. 10, 2013, 12 pages.
Williams, R. E. et al., Degradation of explosives by nitrate ester reductases, Biochem Soc Symp. 2001;(68):143-153.
Miura, K. et al., "The effects of unsaturated fatty acids, oxidizing agents and Michael reaction acceptors on the induction of N-ethylmaleimide reductase in *Escherichia coli*: possible application for drug design of chemoprotectors," Methods Find Exp Clin Pharmacol. Apr. 1997;19(3):147-151.
Unemoto, T. et al., "Chemical structures critical for the induction of FMN-dependent NADH-quinone reductase in *Escherichia coli*," Biochimica et Biophysica Acta, Feb. 1992, 1099(2):170-174.

* cited by examiner

*Primary Examiner* — Kade Ariani

(57) ABSTRACT

A method of deactivating an explosive composition being used in a blasting operation, which method comprises exposing the explosive composition to a micro-organism that is indigenous to the environment in which the explosive composition is being used and that is capable of producing an enzyme that degrades the explosive composition, wherein the explosive composition has associated with it a chemical inducing agent that promotes production of the enzyme by the micro-organism.

19 Claims, 13 Drawing Sheets

MICROBIAL DEACTIVATION OF EXPLOSIVE COMPOSITIONS

CROSS REFERENCE TO RELATED APPLICATIONS

This application is a national stage filing under 35 U.S.C. §371 of International Patent Application No. PCT/AU2013/000072, filed Jan. 29, 2013 and entitled "Microbial Deactivation of Explosive Compositions," which claims priority to Australian Patent Application No. 2012900382, filed Feb. 2, 2012 and entitled "Blasting Method," the disclosure of each of which is hereby incorporated by reference in its entirety.

FIELD OF THE INVENTION

The present invention relates to a method of deactivating an explosive composition that is being used in a blasting operation in order to render the explosive composition safe. The invention is based on causing or accelerating metabolism of an explosive composition by naturally occurring (environmentally prevalent) micro-organisms to produce substances that are non-detonable. In this way the explosive composition is rendered safe. Preferably, the substances produced are also less harmful from an environmental perspective than the explosive composition itself.

BACKGROUND TO THE INVENTION

Explosives are used in a significant number of commercial blasting operations, such as mining, quarrying and seismic exploration. In mining and quarrying a detonator is typically used to initiate a cartridged primer charge that in turn detonates bulk explosive. In seismic exploration a relatively small cartridged explosive charge is initiated using a detonator and the shock waves that are generated are monitored and analysed.

When an explosive charge fails to detonate as intended there are obvious safety and security issues. In that event, it may be possible to recover the charge, although this is not always possible for a variety of reasons. For example, in mining applications and seismic exploration where charges or trains of charges are positioned and detonated, recovery of undetonated charges can be difficult, especially when the charge(s) is/are positioned in an underground borehole and the borehole has been backfilled, as is common practice. There are therefore instances where undetonated charges remain unrecovered in the field. In such cases, and as a general point, it would therefore be desirable to render safe any undetonated and unrecovered explosive charges. A variety of approaches to address this need already exist.

By way of example, U.S. Pat. No. 3,948,177, describes an explosive cartridge for underwater blasting which is said to be self-disarming in the event of an underwater misfire. The cartridge comprises a closed shell including an internal conduit. Water external to the cartridge is prevented from flowing into the conduit by a watertight seal. The force of a percussion impact initiation can however break the watertight seal thereby allowing water to flow into the conduit and contact with explosive composition contained. In turn, water can dissolve the (nitrocarbonate) explosive possibly also causing it to flow out of the body of the cartridge. The result is desensitisation. Whilst generally useful, a problem with this approach is that desensitisation is contingent upon some form of specific force associated with a misfire to break the watertight seal. If there is no applied force resulting from a misfire, the cartridge would not be disarmed by the action of water.

Other approaches, such as those described in WO 97/19253 and WO 98/55822, rely on the use of micro-organisms to effect bio-remediation of an explosive composition in the event that the composition is not detonated as intended. According to these disclosures suitable micro-organisms are included within an explosive composition contained in an explosive device. In other words the micro-organisms are intrinsic to the device. However, such approaches are not without practical complexities. Being biological in nature, care needs to be taken to provide the micro-organisms in a form that is active or that has potential to be active, and care needs to be taken not to destroy the micro-organism thereby rendering them useless. It will also be necessary to supply the micro-organisms with suitable nutrients/metabolites in order to sustain them when they are required to be active. Approaches using micro-organisms contained by design within explosive devices may also lead to unwanted introduction or leakage of possibly exotic micro-organisms and/or chemicals into the environment. Thus, the use of micro-organisms in this context is not without problems.

The present invention seeks to provide an alternative approach to rendering safe explosive compositions that does not suffer the disadvantages described above.

SUMMARY OF THE INVENTION

Accordingly, in one embodiment, the present invention provides a method of deactivating an explosive composition being used in a blasting operation, which method comprises exposing the explosive composition to a micro-organism that is indigenous to the environment in which the explosive composition is being used and that is capable of producing an enzyme that degrades the explosive composition, wherein the explosive composition has associated with it a chemical inducing agent that promotes production of the enzyme by the micro-organism.

The present invention may have particular utility in relation to explosive compositions provided in cartridged form. Accordingly, in a related embodiment, the present invention provides a method of deactivating an explosive composition provided in an explosive cartridge, which method comprises exposing the explosive composition to a micro-organism that is indigenous to the environment in which the explosive cartridge is being used and that is capable of producing an enzyme that degrades the explosive composition, wherein the cartridge has associated with it a chemical inducing agent that promotes production of the enzyme by the micro-organism.

In the present specification the chemical inducing agent is also referred to as an "inducer".

The present invention relies on micro-organisms to metabolise explosive compositions, thereby rendering the compositions non-detonable. However, to be clear, the present invention does not involve the manufacture of an explosive composition or cartridge in which a suitably active micro-organism is included in the explosive composition or cartridge as part of the manufacturing process. Rather, the present invention relies on a micro-organism that is indigenous (naturally occurring) to the environment in which the explosive composition is being used and that can be stimulated to produce an enzyme that degrades the explosive composition. The crux of the invention is the association (provision) with the explosive composition of a chemical inducing agent that causes the (indigenous) micro-organism to produce that enzyme when the chemical inducing agent and micro-organism come into contact with each other. By relying on a naturally occurring micro-organism rather than a "manufactured in" micro-organism, the practical problems noted above in relation to WO 97/19253 and WO 98/55822 can be avoided.

It is possible that the explosive composition, or a component of it, may cause the micro-organism to produce the relevant enzyme. However, also to be clear, in the present invention the chemical inducing agent is an entity distinct from the explosive composition itself.

In another embodiment the present invention provides an explosive composition comprising associated with it a chemical inducing agent that is capable of promoting production of an enzyme that degrades the explosive composition by a micro-organism that is indigenous to the environment in which the explosive composition is to be used.

In another embodiment the present invention provides an explosive cartridge comprising an explosive composition, wherein the explosive cartridge has associated with it a chemical inducing agent that is capable of promoting production of an enzyme that degrades the explosive composition by a micro-organism that is indigenous to the environment in which the explosive cartridge is to be used.

The present invention may involve one or more indigenous micro-organisms to produce one or more suitably active enzymes. For simplicity, in the following, reference will be made in the singular to the micro-organism and enzyme.

The reference to any prior art in this specification is not, and should not be taken as, an acknowledgment or any form of suggestion that that prior art forms part of the common general knowledge in Australia.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

BRIEF DESCRIPTION OF THE DRAWINGS

Embodiments of the present invention are illustrated in the accompanying non-limiting figures, in which.

DETAILED DISCUSSION OF THE INVENTION

Figure 1:
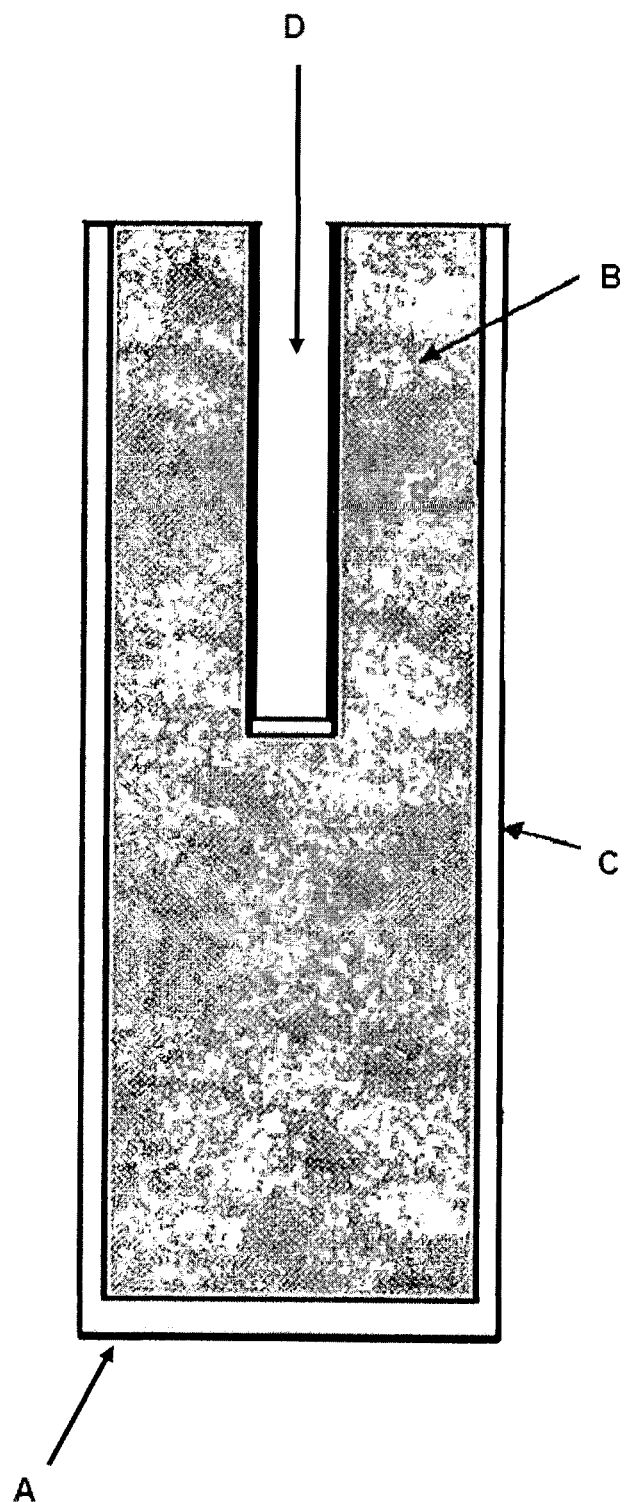
FIG. 1 shows a cross-section of an explosive cartridge in accordance with the present invention.

In accordance with the present invention, the action on the explosive composition of an enzyme produced by an indigenous micro-organism is responsible for rendering the explosive composition insensitive to detonation, i.e. safe. Herein, unless otherwise evident, when it is indicated that an explosive composition is rendered insensitive to detonation means that the explosive composition has, by action of the enzyme, been desensitised at least to the extent that the normal (predetermined) method of initiation of the explosive composition is no longer effective. Thus, for an explosive composition that is known to be detonated using a particular type of initiating device, in accordance with the present invention the explosive composition (charge) is rendered insensitive to detonation if it is no longer possible for it to be initiated in that way. The fact that an explosive composition has been rendered insensitive to detonation does not mean that the explosive charge is completely undetonable (although this is of course a possibility). At the very least, the extent of desensitisation effected by the enzyme in accordance with the invention results in the explosive composition being insensitive to the initiation means that was otherwise and originally intended to cause detonation of the explosive composition. In an embodiment of the present invention, as well as deactivating the explosive composition, the enzyme converts the explosive composition (or components thereof) into one or more compounds that are more environmentally acceptable.

To be clear, the present invention relates to the deactivation of an explosive composition that is being used in a blasting operation but that has not detonated as intended, for whatever reason. It will be appreciated that this context of deactivating an explosive composition is fundamentally different from remediating explosive composition that is present in the environment as a contaminant, for example where there has been unintended spillage or leakage of an explosive composition. Such explosive compositions tend to be somewhat dilute, whereas explosive compositions that are used in the blasting context are more concentrated. Typically, when used in a blasting operation, the explosive composition will be provided in a blasthole. Here the explosive composition may be present as a bulk or packaged product, or in cartridged form as mentioned. Cartridged explosives are commonly used in seismic blasting operations.

In accordance with the present invention the inducer stimulates an indigenous micro-organism to produce an enzyme that is able to degrade the explosive composition, for example present in an explosive cartridge. The inducer may cause the micro-organism to produce the enzyme and in this case the enzyme will not be produced in the absence of the inducer. In an alternative embodiment the micro-organism already produces the enzyme and the inducer stimulates increased and/or prolonged production of the enzyme in order to achieve degradation of the explosive composition.

Central to the present invention is the use of a suitable combination of inducer(s) and (indigenous) micro-organism. It may be necessary to select the inducer(s) that is/are used based on the micro-organism that exists in the environment at the location in which the invention is to be implemented, and based on the activity of that micro-organism with respect to its ability to produce an explosive-degrading enzyme. Alternatively, the invention may be implemented using a broad spectrum inducer, or blend of inducers, that will have the requisite utility with respect to micro-organisms encountered in a particular environment. This latter approach may be simpler to implement and avoids the need to tailor the inducer each time based on the intended site of use of the invention.

One skilled in the art is likely to be familiar with the type of micro-organisms commonly found in the environment and of their potential to express relevant enzymes. This said, one skilled in the art would also be able to indentify micro-organisms that exist at a particular location and assess their usefulness in the context of the present invention.

Examples of micro-organisms that tend to be found in the environment and that produce enzymes that are potentially useful in degrading explosives include *Pseudomonas* spp., *Escherichia coli, Morganella morganii, Rhodococcus* spp., *Comamanos* spp., *Agrobacterium radiobacter, Enterobacter cloacae, Agrobacterium tumifaciens, Klebsiella pneumonia, Gibberella* moniliformis and denitrifying bacteria. Suitable *Pseudomonas* spp. microorganisms include microorganisms in the group aeruginosa, fluorescens, acidovorans, mendocina and cepacia.

Different micro-organisms will of course have propensity to produce different explosive-degrading enzymes. However, by way of example, suitable enzymes may include Old Yellow Enzyme (OYE), oxidoreductases, GTN reductases, nitroreductases (such as NfsA) and N-ethyl maleimide (NEM) reductases.

The inducer may be any compound that promotes the relevant micro-organism to produce (express), or increase its production (regulation) of, an explosive-degrading enzyme. The inducer must also be one that can be conveniently and usefully associated with an explosive cartridge in accordance with the invention.

In an embodiment of the invention the inducer is a Michael acceptor. The Michael reaction involves the addition of a nucleophile (Michael donor) to an α,β-unsaturated compound (Michael acceptor). The latter is known to result in depletion of cellular sulfhydryl groups, and this may trigger an increase in gene expression of relevant enzymes. For example, Michael reaction acceptors such as menadione (vitamin K precursor) and dimethyl maleate are known to up-regulate NEM reductase expression in *E. coli* (Miura et al., 1997). Further examples include N-ethylmaleimide, dimethyl fumarate, diethyl maleate and tert-butyl-hydroquinone.

Michael reaction acceptors are also known to induce mammalian detoxification enzymes, such as quinone reductase, possibly by the same mechanism of cellular sulfhydryl pool depletion (Dinkova-Kostova et al., 1998; Dinkova-Kostova et al., 2001). These compounds (e.g. 3-hydroxy-coumarin, o-coumaric acid and trans-4-phenyl-3-buten-2-one) may also be potential inducers of OYE-like enzymes that are capable of degradation of explosives. The *E. coli* enzyme NADH-quinone reductase is also induced by Michael reaction acceptors, which may potentially have cross-reactivity with explosives (Unemoto et al., 1992). The Examples also identify combinations of inducer and micro-organism that may be suitable for use in practice of the present invention.

In a preferred embodiment the inducer is a Michael acceptor (i.e. an α,β-unsaturated carbonyl compound) and this causes the micro-organism to express an oxidoreductase enzyme that is capable of explosives degradation.

A variety of factors should be taken into account when selecting the inducer to be used and the amount of that inducer. For example, the inducer must be suitably stable (and thus active with respect to a corresponding micro-organism) under the prevailing conditions of intended use. Also, the inducer must be stable with respect to other reagents that in use it will be required to come into contact with, for example to water and/or the explosive composition itself.

The amount (dosage rate) of the inducer should be high enough to illicit the desired response in the relevant micro-organism, but not so high that the inducer will inhibit growth of the micro-organism. If the inducer will be carried by water, dilution effects will also need to be taken into account.

The duration of effectiveness of the inducer may also need to be considered. If the inducer is effective for only a short period, this may be inadequate to achieve the extent of explosive degradation that is necessary. The dosage regime and/or the manner in which the inducer is provided may be relevant to this issue.

It may also be necessary to include in association with the explosive cartridge a suitable nutrient source to support growth of the micro-organism and expression of the explosive-degrading enzyme. Suitable nutrient(s) may be included in the walls of the explosive cartridge. For example, the cartridge may be formed of a starch-based polymer that promotes growth of the micro-organism. Additionally or alternatively, a carbohydrate source (e.g. glucose) or other nutrients (e.g. yeast extract) could be included within the explosive composition (e.g. Pentolite). Such species may be readily soluble however, and prone to leaching out, and this may need to be taken into account.

Supporting micro-organism growth is desirable as it will increase the population and lead to increased rate of expression of relevant enzyme. This may further provide controlled release of enzyme proportional to micro-organism activity.

It may be particularly desirable to encourage micro-organism growth in or immediately adjacent to the explosive composition.

In accordance with the present invention in the event that an explosive composition of the invention fails to fire as intended, the inducer associated with the explosive composition stimulates an indigenous micro-organism to produce, or increase its production of, an enzyme that will degrade the explosive composition. To do this the enzyme must come into contact with the explosive composition. This may occur simply by virtue of the explosive composition being present in a location in which the micro-organism is present. For example, when the explosive composition is a bulk explosive loaded in a blasthole, the relevant micro-organism(s) may also be present in the blasthole, such as in water present in the blasthole or in the ground through which the blasthole extends. When the explosive composition is present in a cartridge this requirement may have implications with respect to design of the explosive cartridge and the manner in which the inducer is associated with the explosive cartridge.

In an embodiment of the invention the inducer may be provided in the explosive composition as a distinct component, for example in the form of particles, pellets, granules, or the like. It is important however that when provided in the explosive composition in this way that the inducer does not interfere with the intended function and performance of the explosive composition. The inducer may be encapsulated to prevent such adverse interaction.

For the invention to be effective, an indigenous micro-organism must come into contact with the inducer present in the explosive composition. In the case of a bulk explosive provided in a blasthole this may inevitably occur. In the case of an explosive cartridge, conveniently, the micro-organism may be transported into the explosive cartridge by water present in the environment. In this case the cartridge will be designed to allow ingress of water. Various design possibilities may permit for this, as will be explained below.

The explosive cartridge may include one or more inlets (apertures) and/or water-degradable pathways to allow environmental water to flow into the cartridge and directly into contact with the explosive composition and the inducer provided in the explosive composition. The explosive composition may itself include channels to allow water to travel through it and into contact with the inducer. The channels may be artificially formed in the explosive composition and/or be naturally occurring given the nature of the explosive composition and the manner in which the explosive composition is loaded into the explosive cartridge. With respect to the latter case, if the explosive composition is loaded into an empty cartridge above the melting point of the composition and then allowed to solidify subsequently, a network of cracks and fissures may be formed in the solidified explosive composition. Water may migrate through these cracks and fissures.

In one embodiment the cartridge may include a water-permeable or water-degradable outer shell (membrane) surrounding the explosive composition, possibly with channels or passages extending into the explosive composition. In use water permeates or degrades the shell (and channels/passages when present) thereby allowing the water and micro-organism to come into contact with the inducer in the explosive composition.

In another related embodiment the cartridge may include a shell and optionally channels/passages formed of a material that will be dissolved by water and/or consumed by microorganisms present in the environment in which the cartridge is used.

In these embodiments the time taken for the microorganism to come into contact with the inducer and the rate at which the microorganism acts on the explosive composition as desired (under prevailing conditions of use) is such that deactivation of the cartridge will not be achieved until a predetermined amount of time has elapsed, prior to which the cartridge would normally have been detonated.

Additionally or alternatively, the inducer may be provided in or on (as a coating, for example) one or more outer walls of the cartridge. In this case the wall will usually be in direct contact with the explosive composition and it will need to be water-permeable, water-degradable or water-soluble. In this embodiment water containing a micro-organism will breach the wall(s) of the cartridge and in doing so the micro-organism and inducer will be brought into contact with each other. In this embodiment the explosive composition may be housed in a chamber (shell) the outer walls of which are formed from a water-permeable cardboard or water-degradable or water-soluble plastics-based material. In this case water may also convey the micro-organism into contact with the explosive composition, and the composition may be adapted to enable water to penetrate readily, as described.

In another embodiment, the inducer may be provided in a chamber (compartment) separate from the explosive composition. In use water is intended to enter the chamber thereby bringing an indigenous micro-organism into contact with the inducer. The activated micro-organism then drains out of the chamber and into contact with the explosive composition. The activated micro-organism may also be flushed out of the chamber by further water that has entered the cartridge. The explosive cartridge and components of it are designed to facilitate this embodiment.

The cartridge may be made up of independent components that are adapted to be attached to each other as the cartridge is being loaded with respective components and when used in the field. By way of example, the explosive composition may be provided in a chamber that is adapted to be secured to another component comprising a chamber for the inducer. The chamber for the inducer may be of single piece construction, for example formed by injection moulding of a suitable plastics material, and include at least one detonator receiving channel as part of the construction. The chamber for the inducer may be provided as part of a cap well or lid piece for the chamber housing the explosive composition. The individual components may be attached to each other by any suitable mechanism, such as interference (friction) fit, male-female screw threading or clip fitting. In this case the explosive composition may be loaded into the respective chamber and the lid secured to the top of the explosive composition chamber. If the explosive composition is a fluid, the attachment must be such that loss of explosive composition is prevented. However, if the explosive composition is solid in nature, for example when the explosive composition is cast hot and allowed to solidify, the attachment may be loose fitting, and this may be beneficial in terms of allowing water to enter the cartridge, as will be explained. The cap well (lid piece) will also generally include a lid/seal over its open end, and this may also allow water to enter the cartridge.

As a further alternative, rather than relying on separate chambers that are integrally formed as parts of the cartridge structure, the inducer and/or explosive composition may be provided in independent containers that are inserted into a rigid cartridge body. In this case it will be appreciated that the cartridge is made up of at least two independent parts and that in use the cartridge is assembled from those parts. Again, however, water ingress is important to the relevant micro-organism contacting the inducer.

Combinations of these various approaches may be used.

The explosive composition used in the explosive cartridge of the invention is conventional in nature and will be selected based on its ability to be desensitised by the deactivation agent or agents to be used. Examples of explosive materials that may be considered for use in the present invention include nitroglycerin (NG), trinitrotoluene (TNT), pentaerythritol tetranitrate (PETN), cyclotrimethylene trinitramine (RDX) and cyclotetramethylene tetranitramine (HMX). The explosive composition may be an emulsion explosive, a water-gel explosive or an ANFO or other nitrate-based composition. Other less conventional explosives may also be used such as liquid or gel compositions which are aqueous or non-aqueous and possible containing other explosive components such as perchlorates. Combinations of explosive materials may also be used. For example, the explosive composition may be Pentolite, a mixture of PETN and TNT. The explosive composition may also contain other explosive and/or reactive ingredients, such as RDX and metallic (e.g. aluminium) particles.

In one embodiment of the present invention the explosive composition may be a water-in-oil emulsion. Emulsion explosive compositions typically include a discontinuous phase comprising a supersaturated aqueous solution of an oxidiser salt (usually ammonium nitrate) dispersed in a continuous oil (fuel) phase. Such emulsions are usually formed by mixing the components in the presence of a suitable emulsifier. In the context of emulsion explosive compositions, the enzyme may be capable of breaking or rendering unstable the emulsion, thereby causing it to be insensitive to detonation. The enzyme may have the effect of causing crystallisation of the supersaturated emulsion component (the oxidiser salt in the type of emulsions described). Accordingly, one skilled in the art may select suitable reagents for use as inducer/micro-organism/enzyme, at least for initial screening, based on a general knowledge of emulsion chemistry and of reagents that are known to cause unwanted crystallisation of (supersaturated) emulsion explosive compositions.

The material(s) used to form the cartridge of the invention should not be corroded by or be reactive towards the inducer formulation employed and explosive composition to be contained. Thus, the cartridge will retain its structural integrity.

With respect to use of a detonator, the cartridge is usually adapted to receive the detonator in a suitably shaped passage extended axially within the body of the cartridge. The cartridge may be adapted to receive a single detonator or more than one detonator in respective, suitably shaped passages. In this regard it should be understood that explosive cartridges for use in seismic exploration, for example, generally allow inclusion of two detonators, a primary detonator and a secondary (back-up) detonator in case the primary detonator does not detonate as intended.

In certain embodiments described, the inducer and indigenous micro-organism will come into contact with each other straight away. In this case the micro-organism may produce an enzyme that will start acting upon the explosive composition immediately. However, in such embodiments for the explosive composition to have a period of usefulness, it is important that the enzyme does not render the explosive composition insensitive to detonation, or reduce significantly the energy output of the explosive composition, immediately. If it did, the explosive composition would be useless, or of little practical use. It is instead intended that the enzyme desensitises the explosive composition after a suitable period of time and by this is meant a period of time after which detonation should otherwise have occurred. Thus, even after production of the enzyme, the explosive composition may need to remain fully detonable (with the energetic output of the explosive composition unaffected or substantially unaffected) for a predetermined period. That period may vary from application to application. For example, when the explosive composition is a bulk explosive, such as an emulsion explosive, the period may be from say two weeks to a month. However, when the explosive composition is provided in an explosive cartridge as is the case for seismic applications) the period may be substantially longer, for example at least about three months and possibly as long as a year, depending upon practical considerations relating to that context of use. The reaction kinetics associated with the enzyme and explosive composition will dictate the rate of which the explosive composition is desensitised. In such embodiments to achieve a useful product the reaction is relatively slow so that the transition between the explosive composition being detonable and non-detonable may be a relatively long one.

The present invention has particular utility in seismic survey applications and in this case the explosive cartridge takes the form of a seismic charge. One skilled in the art will be familiar with the type of explosives in this context.

In an embodiment of the invention the explosive composition may also have associated with it a reagent (e.g. a surfactant) that destabilises or solubilises at least part of the explosive composition. It is believed that this may enhance the deactivating activity of the enzyme. The surfactant may be provided in the explosive composition or it may be provided separately, for example in a separate container with the surfactant being released at an appropriate time. In this embodiment it is obviously important that the surfactant does not interfere with intended functionality of the composition as an explosive. Again, the explosive composition is intended to retain functionality for a period of time in which normal use should have taken place in the normal course of events. The surfactant may be non-ionic, ionic or zwitterionic (amphoteric). The efficacy of a given surfactant may be assessed by experiment. Examples of surfactants that may be used include Brij-35 (or Brij L23), Tween 20/Tween 80, Triton X100, Nonidet P-40 and IGEPAL CA-630 (octylphenoxypolyethoxyethanol), Genapol X-080, Petro® AG (sodium alkylnaphthalene sulphonate), SDS (sodium dodecyl sulphate), Sodium stearate, CHAPS (3-[(3-cholamidopropyl)dimethylammonio]-1-propanesulfonate), CAPB (cocamidopropyl betaine)/cocamidopropyl hydroxysultaine (CAHS) AND Lecithin (L-α-Phosphatidylcholine).

FIG. 1 illustrates an explosive cartridge (A) that could be used as a degradable Pentolite booster. The cartridge includes an explosive composition (B) such as Pentolite surrounded by a shell casing (C) formed of a degradable polymer. The casing (C) may include a suitable inducer based on the micro-organisms that will be present in the environment in which the cartridge (A) is to be used. The cartridge (A) also includes a well (D) extending into the explosives composition (B). The explosive composition (B) may include carbohydrates or other nutrients to promote growth of relevant micro-organisms. A variety of possibilities exist in relation to how the inducer is provided.

1 The inducer could be provided within the explosives composition (B), for example as beads or granules. In this case water will typically be relied upon to transport an indigenous micro-organism into contact with the inducer/explosive composition. In this regard, the casing (C) may be provided with apertures and/or it may be formed from water-permeable, water-degradable or water-soluble material. Water may also enter the well (D) and contact the inducer/explosive composition by that route. The walls and floor of the well may include one or more apertures and/or be formed of a water-permeable, water-degradable or water-soluble material. The explosive composition (B) may also include fissures and/or water-permeable structures to allow easy access of water throughout the composition.
2. The inducer could be provided in the well (D). Water may enter the well (D) through apertures in the cartridge lid (not shown). The well (D) may have the design features noted in 1 above.
3. The inducer may be provided in and/or on (as a coating on) the casing (C), or a part of the casing (C). The casing (C) may be degraded by or permeable to water. Alternatively, the casing (C) may be digested by an indigenous micro-organism. In either embodiment the micro-organism will come into contact the inducer and breach the casing (C) thereby allowing explosive-degrading enzyme produced by the micro-organism to contact the explosive composition.

Combination of embodiments 1, 2 and 3 may also be employed.

Figure 2:
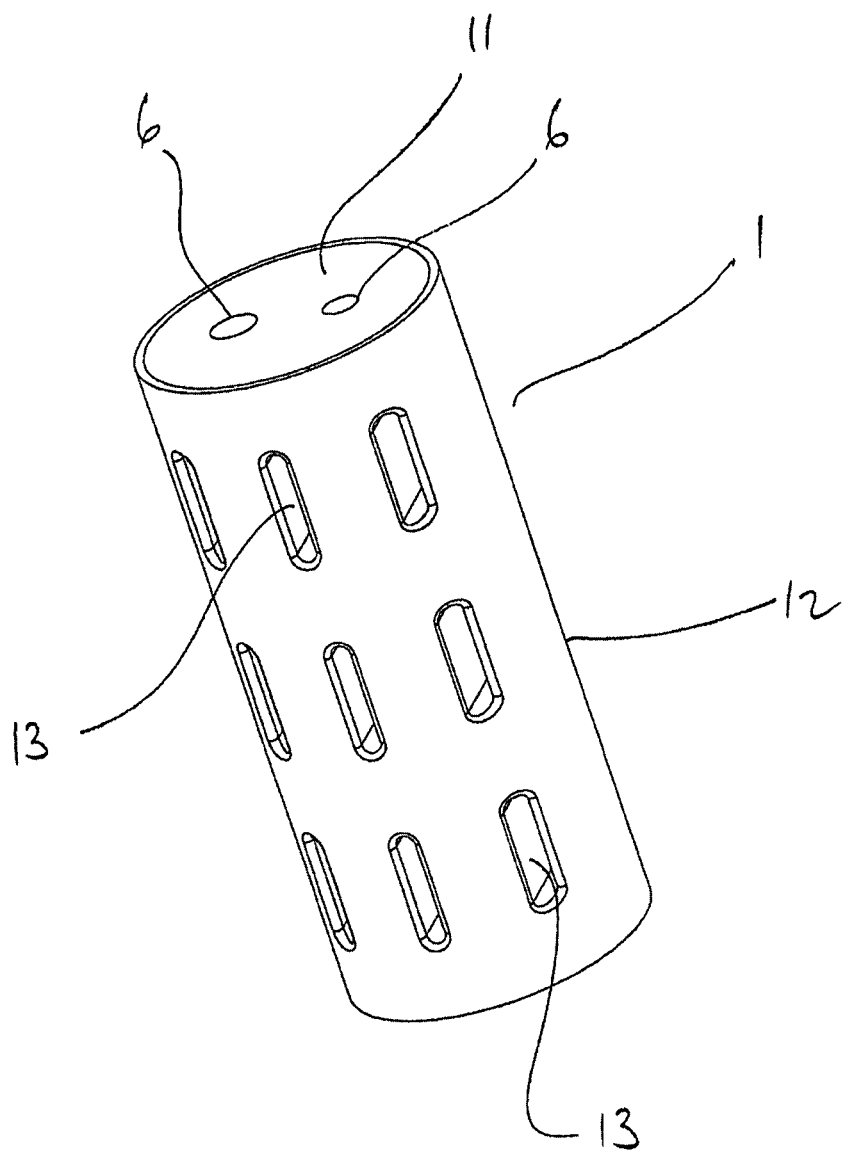
FIGS. 2 and 3 are perspective views of explosive cartridges in accordance with the present invention.

FIG. 2 shows an explosive cartridge (1) useful in implementation of the invention. The cartridge (1) includes explosive composition (11) which typically is in a solid (cast) form, such as Pentolite (typically a PETN/TNT and/or RDX mix). The explosive composition (11) includes detonator receiving channels (6) that enable the cartridge to be initiated by different sized (diameter) detonators. The cartridge (1) includes an outer shell (12) that is made of a water-permeable, water-soluble or water-degradable material. In the field, environmental water will thus permeate or degrade the shell. The shell (12) also defines passages (13) extending into the explosive composition (11). The use of this configuration and type of shell allows environmental water to come into contact with the explosive composition (11), and is thus useful in embodiments of the invention where this is intended/required. The inducer may be provided in the explosive composition (11) and/or in or on the shell (12).

Figure 3:
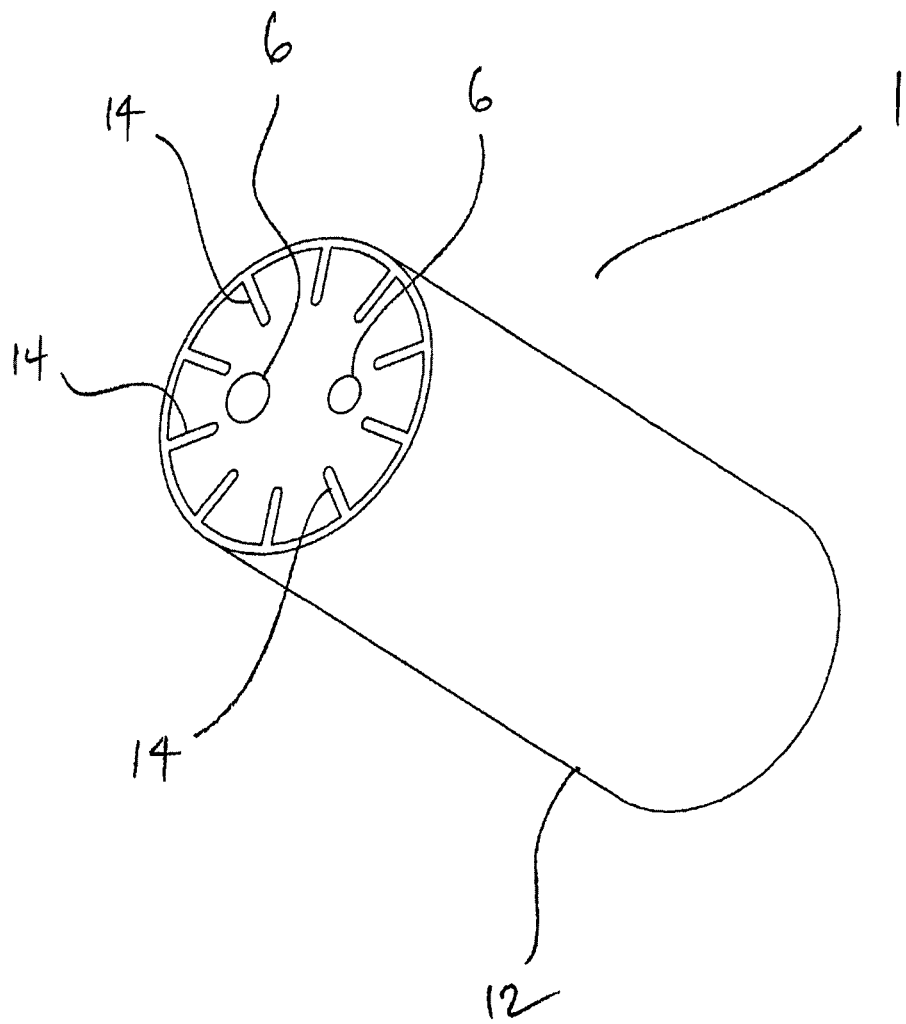

FIG. 3 shows another form of an explosive cartridge (1) useful in implementation of the invention. The cartridge (1) includes an explosive composition (11), such as a cast Pentolite explosive, surrounded by a shell (12). The shell (12) is water-permeable, water-soluble or water-degradable, as for the shell discussed in FIG. 2. In FIG. 3, the shell (12)

includes radial members (14) extending into the bulk of the explosive composition. The intention here is that when the cartridge (1) comes into contact with water, the shell (12) is breached so that water is conveyed into contact with and through the explosive composition, as required by certain embodiments of the invention described herein. The rate at which the shell (12) is breached may be controlled by suitable selection of material used to form the shell (12). Again, the inducer may be provided in the explosive composition (11) and/or in or on the shell (12) and/or in or on the radial members (14).

Figure 4:
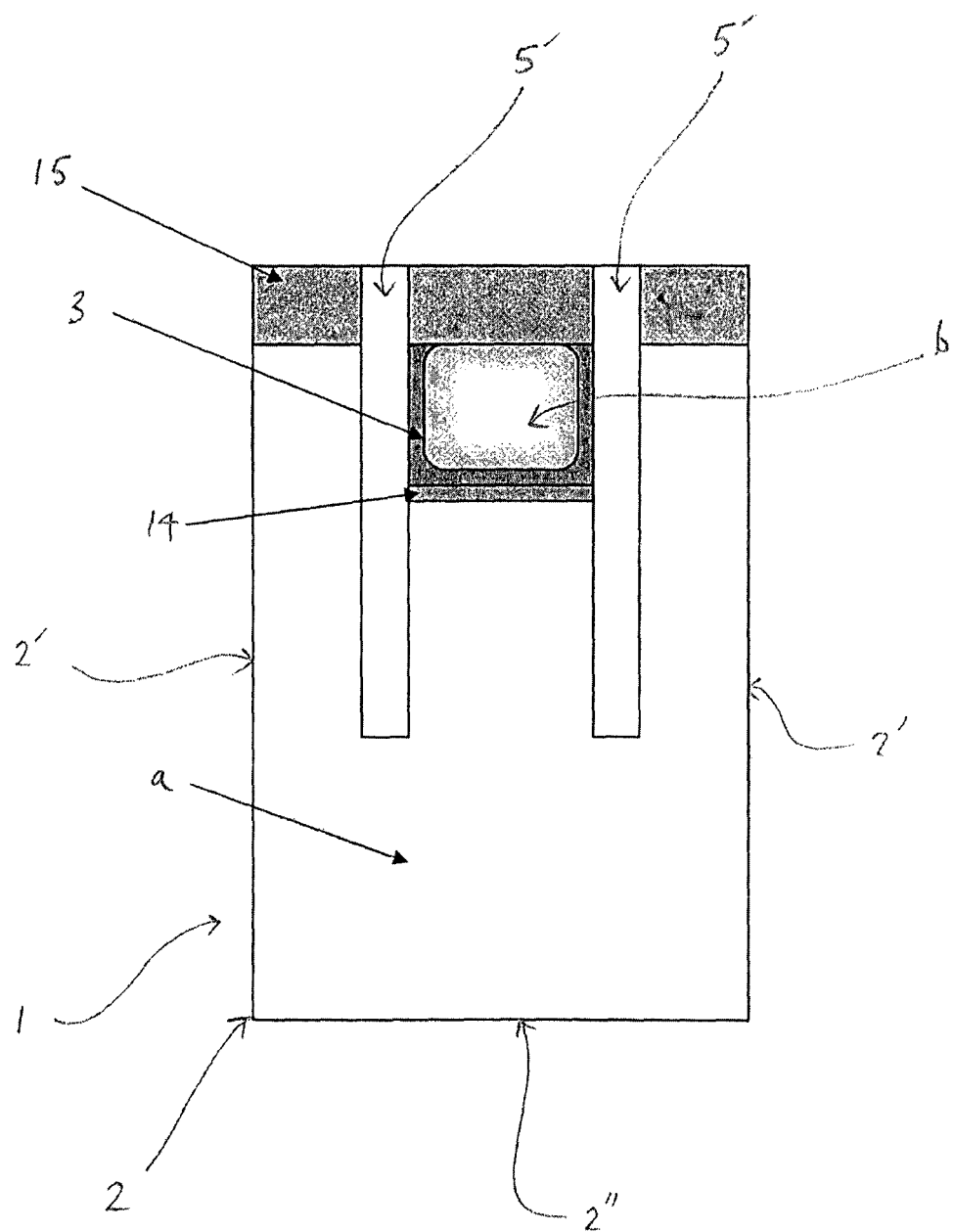
FIG. 4 is a cross-section of an explosives cartridge in accordance with the present invention.

FIG. 4 shows an explosive cartridge (1) that is a variant of the one shown in FIG. 1. In FIG. 4 the explosive cartridge (1) is suitable for use in seismic exploration. The cartridge (1) includes an explosive composition (a) and inducer (b) in respective chambers (2, 3). The chamber for the explosive composition (a) is in the form of a cylindrical shell comprising wall portions (2') sealed by a base (2"). The explosive composition (a) may be Pentolite, possibly in mixture with RDX and/or aluminium particles.

The explosive composition (a) and inducer (b) are separated in their respective chambers by a base plate (14) that is loosely fitted at the lower end of the chamber (3) for the inducer (b). The plate (14) may be formed of any suitable material such as a polyester or polycarbonate. That said, depending upon the nature of the inducer and explosive composition it may be possible to dispense with the plate (14) altogether.

The cartridge (1) also includes two detonator receiving channels (5') extending into the explosive composition (a). The cartridge (1) also includes a cap (15) at one end. This cap (15) is sized and shaped to fit, for example by interference fit, into the shell housing the explosive composition.

Figure 5:
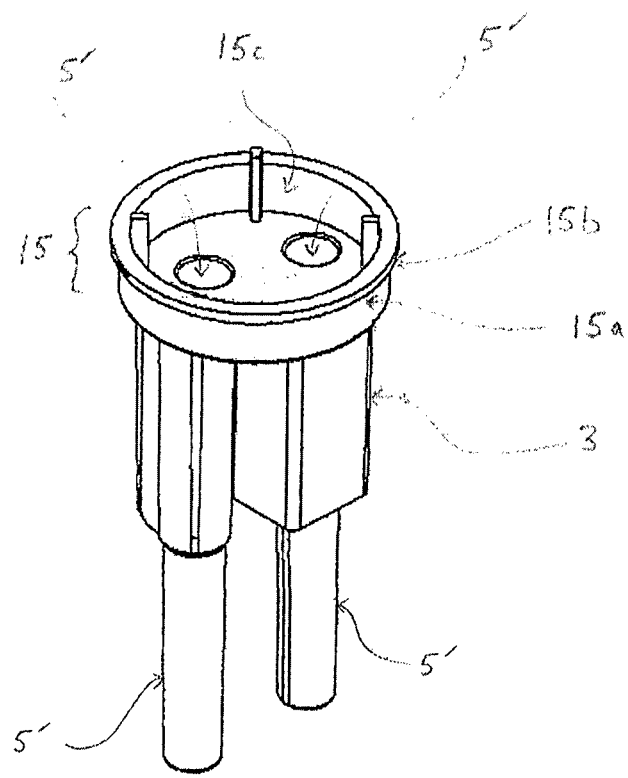
FIGS. 5 and 6 are perspective views showing a component of the explosives cartridge depicted in FIG. 3.
Figure 6:
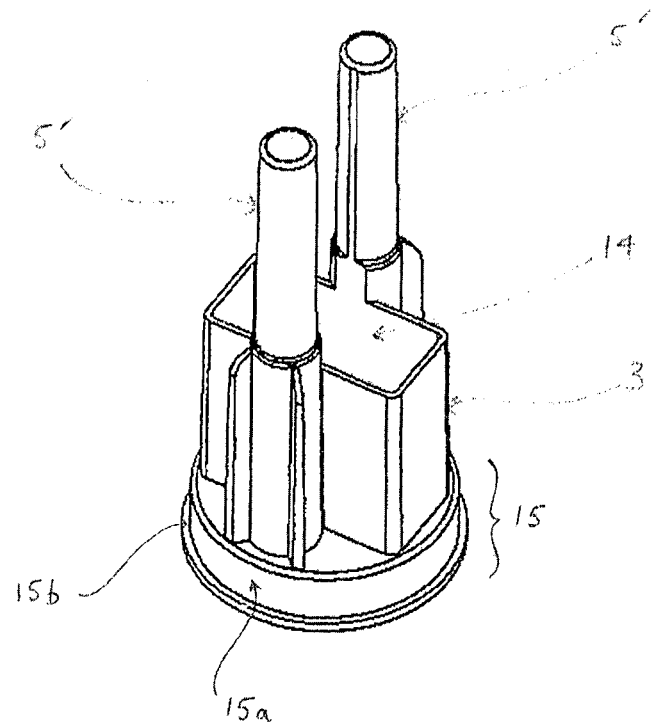

In practice the cartridge (1) may be provided as separate components that are assembled during loading of respective components and when used in the field. With respect to FIG. 4, one component may be integrally formed (by injection moulding of a plastic material) to include and define, the cap (15), the detonator receiving channels (5') and the chamber (3) for the inducer (b) as illustrated in FIGS. 5 and 6. The base plate (14) and chamber/shell (2) for the explosive composition (a) are separate components. The chamber (2) is made up of a cylindrical tube comprising wall portions (2') and a base (2") that is attached at a lower end of the tube thereby sealing it.

FIGS. 5 and 6 illustrate certain components shown in FIG. 4. Thus, FIGS. 5 and 6 show the cap (15), detonating receiving channels (5') and chamber (3) for the inducer formed as a one-piece construction, for example by injection moulding of a suitable plastic material. The chamber (3) for the inducer is sealed by a separate plate (14). The cap (15) comprises a circular wall portion (15a) with a lip (15b) that enables the cap (15) to be secured (by interference fit) into a suitably sized and shaped chamber in which an explosive composition is provided (not shown in FIGS. 5 and 6). The cap (15) is typically inserted into a tube forming. The wall portions (2' in FIG. 4) extend above and below the cap (15) once inserted and are adapted to allow attachment of other cartridges or a nose cone, for example by thread fitting. The internal surface of the wall portion (2') may include a lug or tab to engage the lip (15b) so as to maintain the cap (15) in position. The upper end of the cap (15) is open to allow for insertion of at least one detonator into respective detonator receiving channels (5'). The open end of the cap (15c) may be sealed with a suitably sized and shaped lid (not shown) or be formed in an injection moulding process. The cap (15) and/or wall, portions (2' in FIG. 4) may include apertures to allow water to enter the explosive cartridge. As noted the wall portion (2' in FIG. 4) extending above the position of the cap (15) may receive the lower end of another explosive cartridge to form a train of cartridges. In this regard a surface of the wall portion (2' in FIG. 4) may be threaded to mate with corresponding threads provided on the outer surface and at the base of another cartridge. Cartridges may also be coupled by interference fit or by clip fasteners. The cap (15) may include apertures or grooves (not shown) in the side wall thereof extending through the circular wall portion (15a) and lip (15b) through which detonator leads may be passed after a detonator loading.

The embodiment illustrated in FIGS. 4-6 may be implemented as follows. In the orientation shown in FIG. 6 the plate (14) is removed and inducer inserted into the chamber (3). The plate (14) is then replaced thereby sealing the chamber (3). The seal is loose in the sense that the chamber (3) is not liquid tight. Still in the orientation shown in FIG. 6, a cylindrical tube defining the wall portions (2') of the chamber (2) for the explosive composition (a) is inserted over the cap (15) with the cap (15) being retained in place by interference fit between the wall portion (2') and cap lip (15b).

An explosive composition, such as Pentolite, can then be poured into the open end of the tube, thereby surrounding the chamber (3) and detonator receiving channels (5'). If Pentolite is used it is cast above its melting point and allowed to solidify. Solidification may result in the formation of cracks and fissures extending through the bulk of the explosive composition. This may be desirable as such cracks and fissures allow water to travel through the explosive composition, as may be desired. Once the tube has been suitably filled with explosive composition, and the composition solidified as might be necessary, a base (2") is attached to the open end of the tube. The base (2") and wall portions (2') may form a seal by interference fit, male-female screw threading or by clip fastening.

In use the component so-formed is loaded with one or more detonators with the detonator leads being passed out of the cap (15) or upper part of wall portions (2') as noted. The top end of the cap (15) may itself be sealed using a lid made of water-degradable material (not shown).

In the embodiment described it is intended that the inducer (b) comes into contact with micro-organisms that are carried by water entering the chamber (3) around the edges of the plate (14). The plate may additionally or alternatively include apertures to allow water entry into the chamber (3). Additionally or alternatively, the wall portions of the chamber (3) may also include structures to allow water to enter the chamber (3) (the chamber (3) may itself be made of water-degradable material to facilitate water ingress). The inducer promotes production of explosive degrading enzyme and this then contacts the explosive composition via the same (or different) route through which water entered the chamber (3).

Water may find its way into the chamber (3) in one or a combination of more than one way, as follows.

Where respective components are joined together, for example the wall portions (2') forming the chamber (2) and the cap (15) or the wall portions (2') and base (2"), the joint may allow water ingress. In this case water would enter the chamber (3) around the plate (14) by migration through the bulk of the explosive composition. The composition must therefore allow water transport by the presence of artificial and/or intrinsic water transport structures.

Additionally or alternatively, water may enter the explosive composition through the walls (2') and/or base (2") of the chamber (2). One or both of these components may include channels/apertures to allow water entry and/or one or both may be water-permeable or water-degradable. The exact configuration will depend upon the form of, and thus the containment needs, of the explosive composition.

Additionally or alternatively, water may enter the chamber (3) via the cap (15). Thus, the cap (15) may include channels/apertures extending through the cap (15) and into the chamber (3), for example through an aperture between the inner surface (15c) and the chamber (3). The aperture may itself be sealed by water-soluble, water-permeable or a water-degradable material. Water may enter the cap (15) through loose fitting seals (between the cap (15) and cap lid or between the wall portion (2') and an adjacent cartridge when a train of multiple cartridges is assembled). The apertures/grooves for the detonator leads may also allow water to enter the cap. Apertures/grooves in the upper part of the wall portions (2') may also allow water ingress.

One or more components of the cartridge may be water-degradable, and the degradability may be selective in order to provide enhanced control with respect to intended deactivation of the explosive composition.

Embodiments of the present invention are illustrated in the following non-limiting examples.

EXAMPLE 1

Induction of nitroglycerin-Degrading Activity in Escherichia coli DH5α

An overnight culture of Escherichia coli DH5α grown at 30° C. with shaking at 200 rpm in Luria Broth was inoculated 10% v/v (1 mL into 9 mL) into the same medium containing various test compounds and incubated for a further 24 h. The inducer compounds tested were 0.25 mM N-ethylmaleimide (NEM), 0.25 mM menadione (MD), 1 mM dimethyl fumarate (DMFU), 4 mM diethyl maleate (DEME), 4 mM diethyl malonate (DEMO), 4 mM dimethyl malonate (DMMO), 0.5 mM glycerol trinitrate (GTN), 0.5 mM pentaerythritol tetranitrate (PETN) and 0.5 mM trinitrotoluene (TNT). Controls without test compound were included and the media also contained up to 1% v/v ethanol from the inducer stock solutions, which did not affect growth or enzyme expression (or acetone in the case of PETN and TNT). Cells were harvested by centrifugation (3220×g, 15 min, 4° C.), washed in 50 mM potassium phosphate pH 7.2 and the pellets were stored at −20° C. Pellets were resuspended in 1.5 mL of lysis buffer (50 mM Tris pH 8, 100 mM NaCl, 0.5% Triton X-100) and sonicated for 3×15 s pulses at 35% power with 30 s rest between pulses using a Branson Digital Sonifier. Following incubation on ice for at least 1 h, lysates were clarified by centrifugation (16,100×g, 5 min, 22° C.) and the supernatant was used for enzyme assays.

Enzyme activity of cell-free extracts was determined by measuring the formation of nitrite from 0.2 mM nitroglycerin and 0.2 mM NADPH in 50 mM potassium phosphate pH 7.2 at room temperature. Assays were terminated at various time points by addition of 0.2 mM phenazine methosulfate and 0.5 mM ferricyanide. Nitrite concentration was determined by mixing 100 µL of sample with 900 µL of 10 mg/mL nitrite reagent (Sigma, cat#37410) and measuring absorbance at 530 nm after 10 minutes. One unit of activity was defined as the amount of enzyme required to release 1 µmol of nitrite per min from nitroglycerin at room temperature (∼22° C.) and was expressed per gram of protein. Protein concentrations were determined using Bradford reagent (Bio-Rad) according to manufacturer's instructions.

Figure 7:
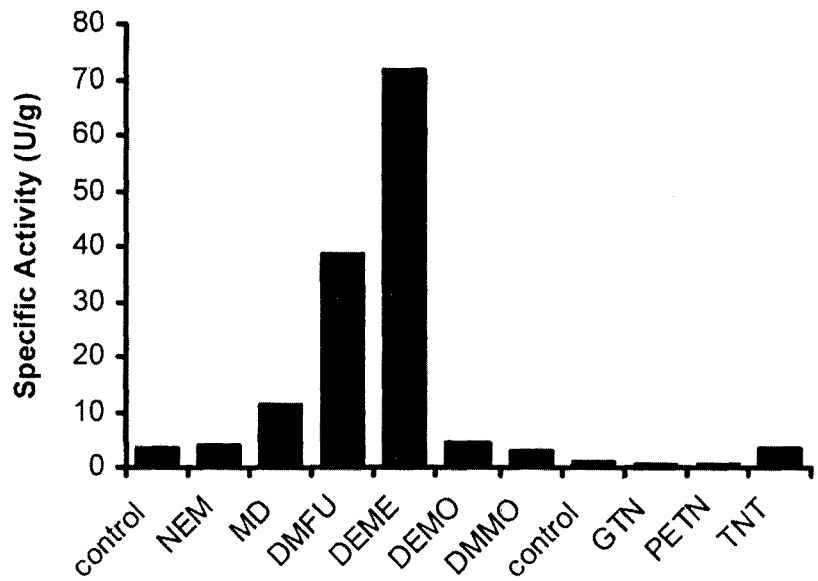
FIGS. 7 to 21 illustrate results obtained in the Examples.

The results are shown FIG. 7 and the table below, which clearly shows an increase in nitroglycerin-degrading activity when E. coli DH5α is exposed to MD, DMFU and DEME with increases of 3.5-, 12- and 22-fold respectively relative to the control. The structurally similar non-Michael acceptors DEMO and DMMO did not illicit any significant response nor did the explosive compounds GTN or PETN. Activity was induced slightly by TNT, however this result is not conclusive as the specific activity of the control in the second preparation was significantly less that for the first preparation indicating a degree of natural variation between samples.

| Chemical | U/g | Fold-Induction |
| --- | --- | --- |
| control | 3.3 | 1.0 |
| NEM | 3.7 | 1.1 |
| MD | 11 | 3.5 |
| DMFU | 38 | 12 |
| DEME | 72 | 22 |
| DEMO | 4.5 | 1.4 |
| DMMO | 3.1 | 1.0 |
| control | 0.8 | 1.0 |
| GTN | 0.44 | 0.5 |
| PETN | 0.26 | 0.3 |
| TNT | 3.4 | 4.2 |

EXAMPLE 2

Induction of nitroglycerin-Degrading Activity in Agrobacterium tumifaciens AGL-1

An overnight culture of Agrobacterium tumifaciens AGL-1 grown at 30° C. with shaking at 200 rpm in Luria Broth was inoculated 10% v/v (1 mL into 9 mL) into the same medium containing various test compounds and incubated for a further 24 h. The inducer compounds tested were 0.25 mM N-ethylmaleimide (NEM), 0.125 mM menadione (MD), 1 mM dimethyl fumarate (DMFU), 4 mM diethyl maleate (DEME), 4 mM diethyl malonate (DEMO), 4 mM dimethyl malonate (DMMO), 0.5 mM glycerol trinitrate (GTN), 0.5 mM pentaerythritol tetranitrate (PETN) and 0.5 mM trinitrotoluene (TNT). Controls without test compound were included and the media also contained up to 1% v/v ethanol from the inducer stock solutions, which did not affect growth or enzyme expression (or acetone in the case of PETN and TNT). Cells were harvested by centrifugation (3220×g, 15 min, 4° C.), washed in 50 mM potassium phosphate pH 7.2 and the pellets were stored at −20° C. Pellets were resuspended in 1.5 mL of lysis buffer (50 mM Tris pH 8, 100 mM NaCl, 0.5% Triton X-100) and sonicated for 3×15 s pulses at 35% power with 30 s rest between pulses using a Branson Digital Sonifier. Following incubation on ice for at least 1 h, lysates were clarified by centrifugation (16,100×g, 5 min, 22° C.) and the supernatant was used for enzyme assays.

Enzyme activity of cell-free extracts was determined by measuring the formation of nitrite from 0.2 mM nitroglycerin and 0.2 mM NADH in 50 mM potassium phosphate pH 7.2 at room temperature. Assays were terminated at various time points by addition of 0.2 mM phenazine methosulfate and 0.5 mM ferricyanide. Nitrite concentration was determined by mixing 100 µL of sample with 900 µL of 10 mg/mL nitrite reagent (Sigma, cat#37410) and measuring absorbance at 530 nm after 10 minutes. One unit of activity was defined as the amount of enzyme required to release 1 µmol of nitrite per min from nitroglycerin at room temperature (~22° C.) and was expressed per gram of protein. Protein concentrations were determined using Bradford reagent (Bio-Rad) according to manufacturer's instructions.

Figure 8:
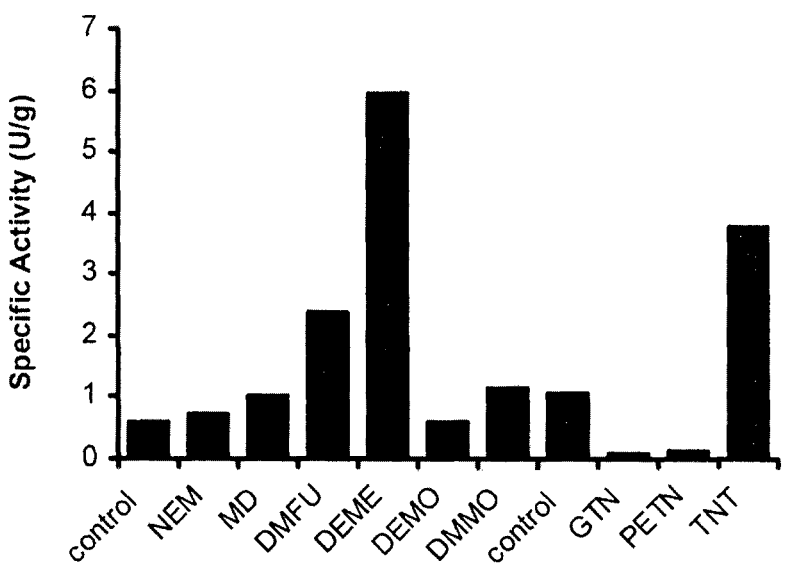

The results are shown in FIG. 8 and the table below, which clearly shows an increase in nitroglycerin-degrading activity when *A. tumifaciens* AGL-1 is exposed, to DMFU and DEME with increases of 4.0- and 9.9-fold respectively relative to the control. The structurally similar non-Michael acceptors DEMO and DMMO did not illicit any significant response nor did the explosive compounds GTN or PETN. However, the explosive compound TNT did significantly increase enzyme activity in this strain. This may be due to the toxicity of TNT resulting in a stress response that involves up-regulation of nitroglycerin-degrading reductases. This strong response appears to be a unique characteristic of this strain.

| Chemical | U/g | Fold-Induction |
| --- | --- | --- |
| control | 0.60 | 1.0 |
| NEM | 0.72 | 1.2 |
| MD | 1.0 | 1.7 |
| DMFU | 2.4 | 4.0 |
| DEME | 5.9 | 9.9 |
| DEMO | 0.60 | 1.0 |
| DMMO | 1.1 | 1.9 |
| control | 1.1 | 1.0 |
| GTN | 0.10 | 0.07 |
| PETN | 0.14 | 0.14 |
| TNT | 3.8 | 3.5 |

EXAMPLE 3

Induction of nitroglycerin-Degrading Activity in *Agrobacterium tumifaciens* PD31

An overnight culture of *Agrobacterium tumifaciens* PD31 grown at 30° C. with shaking at 200 rpm in Luria Broth was inoculated 10% v/v (1 mL into 9 mL) into the same medium containing various test compounds and incubated for a further 24 h. The inducer compounds tested were 0.5 mM N-ethylmaleimide (NEM), 0.25 mM menadione (MD), 1 mM dimethyl fumarate (DMFU), 4 mM diethyl maleate (DEME), 4 mM diethyl malonate (DEMO), 4 mM dimethyl malonate (DMMO), 0.5 mM glycerol trinitrate (GTN), 0.5 mM pentaerythritol tetranitrate (PETN) and 0.5 mM trinitrotoluene (TNT). Controls without test compound were included and the media also contained up to 1% v/v ethanol from the inducer stock solutions, which did not affect growth or enzyme expression (or acetone in the case of PETN and TNT). Cells were harvested by centrifugation (3220×g, 15 min, 4° C.), washed in 50 mM potassium phosphate pH 7.2 and the pellets were stored at −20° C. Pellets were resuspended in 1.5 mL of lysis buffer (50 mM Tris pH 8, 100 mM NaCl, 0.5% Triton X-100) and sonicated for 3×15 s pulses at 35% power with 30 s rest between pulses using a Branson Digital Sonifier. Following incubation on ice for at least 1 h, lysates were clarified by centrifugation (16,100×g, 5 min, 22° C.) and the supernatant was used for enzyme assays.

Enzyme activity of cell-free extracts was determined by measuring the formation of nitrite from 0.2 mM nitroglycerin and 0.2 mM NADH in 50 mM potassium phosphate pH 7.2 at room temperature. Assays were terminated at various time points by addition of 0.2 mM phenazine methosulfate and 0.5 mM ferricyanide. Nitrite concentration was determined by mixing 100 µL of sample with 900 µL of 10 mg/mL nitrite reagent (Sigma, cat#37410) and measuring absorbance at 530 nm after 10 minutes. One unit of activity was defined as the amount of enzyme required to release 1 µmol of nitrite per min from nitroglycerin at room temperature (~22° C.) and was expressed per gram of protein. Protein concentrations were determined using Bradford reagent (Bio-Rad) according to manufacturer's instructions.

Figure 9:
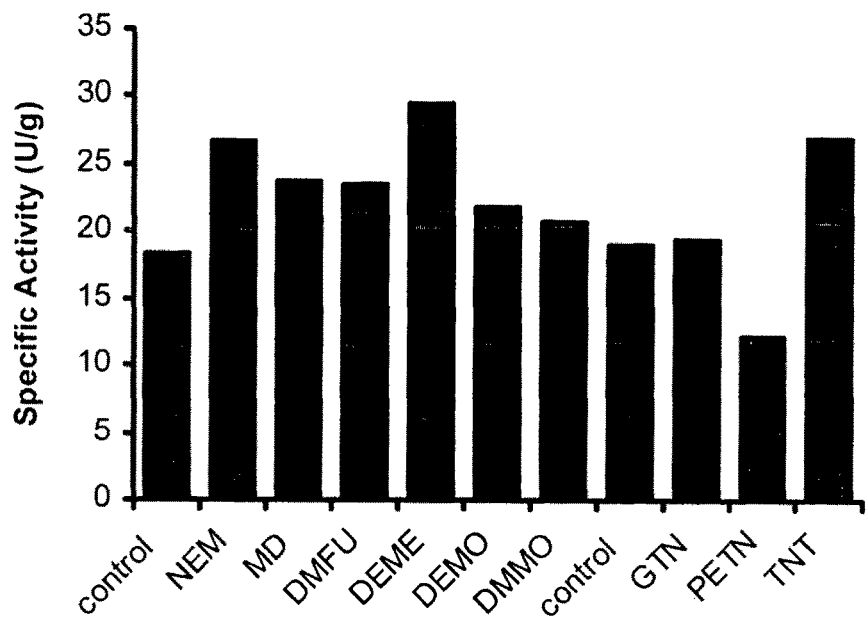

The results are shown in FIG. 9 and the table below, which shows a slight increase in nitroglycerin-degrading activity when *A. tumifaciens* PD31 is exposed to NEM, DEME and TNT, but only up to 1.6-fold higher relative to the control. The results indicate that enzyme expression is not as highly regulated in this strain compared to others and so the addition of an α,β-unsaturated carbonyl compound does not result in a pronounced increase in nitroglycerin-degrading activity. This strain is also a known degrader of PETN and TNT, which was isolated from soil using PETN as the sole source of nitrogen. Deregulation of this enzyme accompanied with relatively high basal expression levels may explain why this isolate became the predominant strain in a mixed soil consortium following several passages with PETN as the sole nitrogen source.

| Chemical | U/g | Fold-Induction |
| --- | --- | --- |
| control | 18 | 1.0 |
| NEM | 27 | 1.5 |
| MD | 24 | 1.3 |
| DMFU | 24 | 1.3 |
| DEME | 29 | 1.6 |
| DEMO | 22 | 1.2 |
| DMMO | 21 | 1.1 |
| control | 19 | 1.0 |
| GTN | 19 | 1.0 |
| PETN | 12 | 0.64 |
| TNT | 27 | 1.4 |

EXAMPLE 4

Induction of nitroglycerin-Degrading Activity in *Klebsiella pneumoniae* BB6

An overnight culture of *Klebsiella pneumoniae* BB6 grown at 30° C. with shaking at 200 rpm in Luria Broth was inoculated 10% v/v (1 mL into 9 mL) into the same medium containing various test compounds and incubated for a further 24 h. The inducer compounds tested were 0.5 mM N-ethylmaleimide (NEM), 0.5 mM menadione (MD), 1 mM dimethyl fumarate (DMFU), 4 mM diethyl maleate (DEME), 4 mM diethyl malonate (DEMO), 4 mM dimethyl malonate (DMMO), 0.5 mM glycerol trinitrate (GTN), 0.5 mM pentaerythritol tetranitrate (PETN) and 0.5 mM trinitrotoluene (TNT). Controls without test compound were included and the media also contained up to 1% v/v ethanol from the inducer stock solutions, which did not affect growth or enzyme expression (or acetone in the case of PETN and TNT). Cells were harvested by centrifugation (3220×g, 15 min, 4° C.), washed in 50 mM potassium phosphate pH 7.2 and the pellets were stored at −20° C. Pellets were resuspended in 1.5 mL of lysis buffer (50 mM Tris pH 8, 100 mM NaCl, 0.5% Triton X-100) and sonicated for 3×15 s pulses at 35% power with 30 s rest between pulses using a Branson Digital Sonifier. Following incubation on ice for at least 1 h, lysates were clarified by centrifugation (16,100×g, 5 min, 22° C.) and the supernatant was used for enzyme assays.

Enzyme activity of cell-free extracts was determined by measuring the formation of nitrite from 0.2 mM nitroglycerin and 0.2 mM NADPH in 50 mM potassium phosphate pH 7.2 at room temperature. Assays were terminated at various time points by addition of 0.2 mM phenazine methosulfate and 0.5 mM ferricyanide. Nitrite concentration was determined by mixing 100 µL of sample with 900 µL of 10 mg/mL nitrite reagent (Sigma, cat#37410) and measuring absorbance at 530 nm after 10 minutes. One unit of activity was defined as the amount of enzyme required to release 1 µmol of nitrite per min from nitroglycerin at room temperature (~22° C.) and was expressed per gram of protein. Protein concentrations were determined using Bradford reagent (Bio-Rad) according to manufacturer's instructions.

Figure 10:
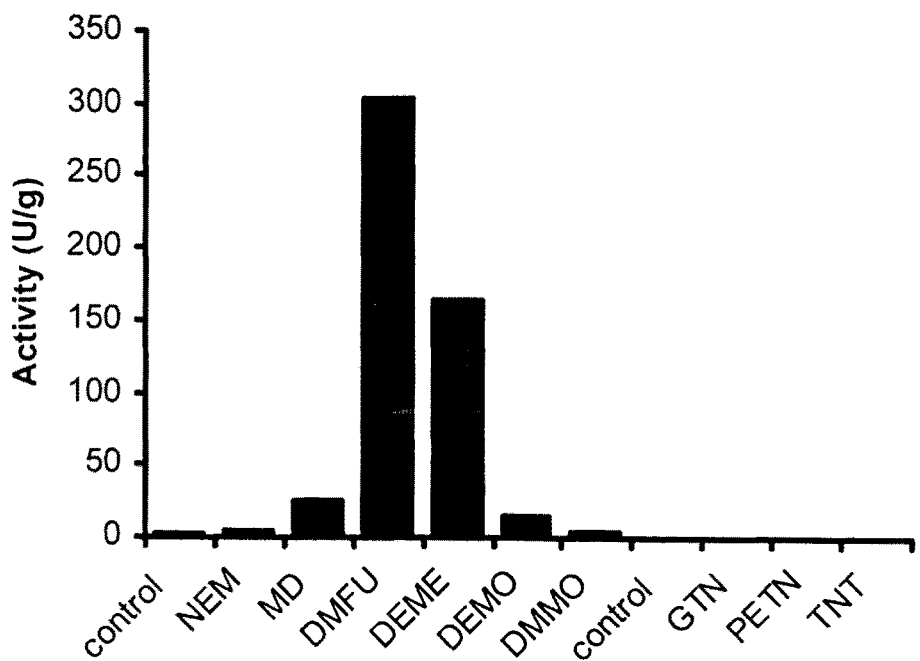

The results are shown in FIG. 10 and the table below, which clearly shows an increase in nitroglycerin-degrading activity when *K. pneumoniae* BB6 is exposed to MD, DMFU and DEME with increases of 8.8-, 106- and 58-fold respectively relative to the control. The very large increases in enzyme activity suggest that gene expression is highly regulated in this strain. The structurally similar non-Michael acceptor DEMO also resulted in a 5.1-fold increase in activity indicating that chemical structure as well as functionality may play a role in enzyme induction in this strain. The explosive compounds GTN, PETN or TNT did not illicit any significant response.

| Chemical | U/g | Fold-Induction |
| --- | --- | --- |
| control | 2.9 | 1.0 |
| NEM | 4.5 | 1.6 |
| MD | 25 | 8.8 |
| DMFU | 303 | 106 |
| DEME | 165 | 58 |
| DEMO | 15 | 5.1 |
| DMMO | 4.6 | 1.6 |
| control | <0.10 | 1.0 |
| GTN | <0.10 | 1.0 |
| PETN | <0.10 | 1.0 |
| TNT | 0.22 | 2.2 |

EXAMPLE 5

Induction of nitroglycerin-Degrading Activity in *Pseudomonas* Sp. BB13

An overnight culture of *Pseudomonas* sp. BB13 grown at 30° C. with shaking at 200 rpm in Luria Broth was inoculated 10% v/v (1 mL into 9 mL) into the same medium containing various test compounds and incubated for a further 24 h. The inducer compounds tested were 0.25 mM N-ethylmaleimide (NEM), 0.5 mM menadione (MD), 1 mM dimethyl fumarate (DMFU), 4 mM diethyl maleate (DEME), 4 mM diethyl malonate (DEMO), 4 mM dimethyl malonate (DMMO), 0.5 mM glycerol trinitrate (GTN), 0.5 mM pentaerythritol tetranitrate (PETN) and 0.5 mM trinitrotoluene (TNT). Controls without test compound were included and the media also contained up to 1% v/v ethanol from the inducer stock solutions, which did not affect growth or enzyme expression (or acetone in the case of PETN and TNT). Cells were harvested by centrifugation (3220×g, 15 min, 4° C.), washed in 50 mM potassium phosphate pH 7.2 and the pellets were stored at -20° C. Pellets were resuspended in 1.5 mL of lysis buffer (50 mM Tris pH 8, 100 mM NaCl, 0.5% Triton X-100) and sonicated for 3×15 s pulses at 35% power with 30 s rest between pulses using a Branson Digital Sonifier. Following incubation on ice for at least 1 h, lysates were clarified by centrifugation (16,100×g, 5 min, 22° C.) and the supernatant was used for enzyme assays.

Enzyme activity of cell-free extracts was determined by measuring the formation of nitrite from 0.2 mM nitroglycerin and 0.2 mM NADPH in 50 mM potassium phosphate pH 7.2 at room temperature. Assays were terminated at various time points by addition of 0.2 mM phenazine methosulfate and 0.5 mM ferricyanide. Nitrite concentration was determined by mixing 100 µL of sample with 900 µL of 10 mg/mL nitrite reagent (Sigma, cat#37410) and measuring absorbance at 530 nm after 10 minutes. One unit of activity was defined as the amount of enzyme required to release 1 µmol of nitrite per min from nitroglycerin at room temperature (~22° C.) and was expressed per gram of protein. Protein concentrations were determined using Bradford reagent (Bio-Rad) according to manufacturer's instructions.

Figure 11:
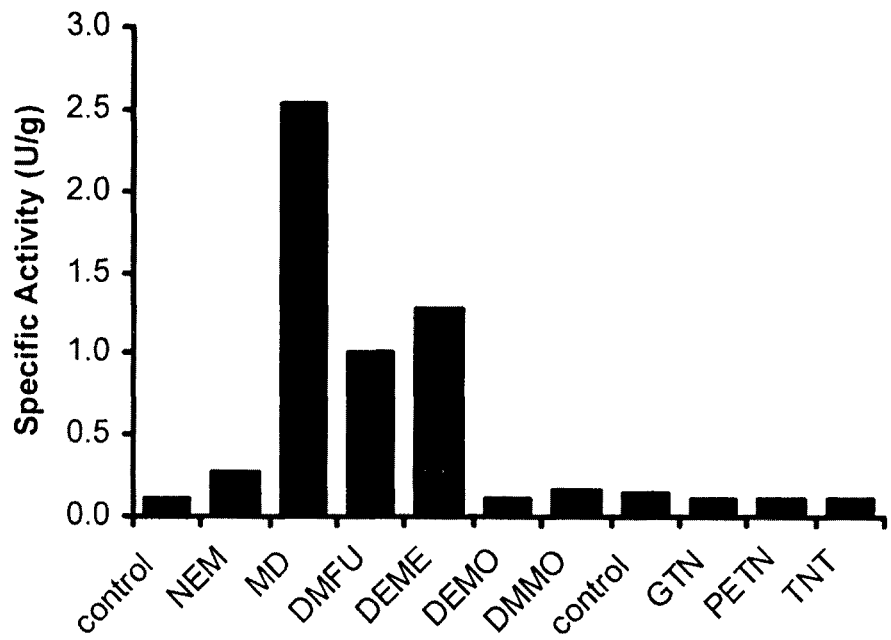

The results are shown in FIG. 11 and the table below, which clearly shows an increase in nitroglycerin-degrading activity when *Pseudomonas* sp. BB13 is exposed to NEM, MD, DMFU and DEME with increases of 2.7-, 25-, 10- and 13-fold respectively relative to the control. The structurally similar non-Michael acceptors DEMO and DMMO did not illicit any significant response nor did the explosive compounds GTN, PETN or TNT.

| Chemical | U/g | Fold-Induction |
| --- | --- | --- |
| control | <0.10 | 1.0 |
| NEM | 0.27 | 2.7 |
| MD | 2.5 | 25 |
| DMFU | 1.0 | 10 |
| DEME | 1.3 | 13 |
| DEMO | 0.11 | 1.1 |
| DMMO | 0.15 | 1.5 |
| control | 0.15 | 1.0 |
| GTN | <0.10 | 0.68 |
| PETN | <0.10 | 0.68 |
| TNT | <0.10 | 0.68 |

EXAMPLE 6

Induction of nitroglycerin-Degrading Activity in *Gibberella moniliformis* CD611

A three day culture of *Gibberella moniliformis* CD611 grown at 30° C. with shaking at 200 rpm in Luria Broth was inoculated 10% v/v (1 mL into 9 mL) into the same medium containing various test compounds and incubated for a further 29 h. The inducer compounds tested were 0.5 mM glycerol trinitrate (GTN), 0.5 mM pentaerythritol tetranitrate (PETN), 0.5 mM trinitrotoluene (TNT), 0.5 mM N-ethylmaleimide (NEM), 0.25 mM menadione (MD), 1 mM dimethyl fumarate (DMFU), 4 mM diethyl maleate (DEME), 1 mM 3-hydroxycoumarin (3HC), 1 mM trans-4-phenyl-3-buten-2-one (TPBO), 1 mM tert-butyl-hydroquinone (TBHQ) and 1 mM dimethyl maleate (DMME). Controls without test compound were included and the media also contained up to 1% v/v ethanol from the inducer stock solutions, which did not affect growth or enzyme expression (or acetone in the case of PETN and TNT). Cells were harvested by vacuum filtration through at Whatman No. 1 filter paper, washed twice with 10 mL of 50 mM potassium phosphate pH 7.2 and the biomass was stored at -20° C. Pellets were resuspended in 1.5 mL of lysis buffer (50 mM Tris pH 8, 100 mM NaCl, 0.5% Triton X-100) and sonicated for 3×15 s pulses at 35% power with 30 s rest between pulses using a Branson Digital Sonifier. Following incubation on ice for 20 min, the sonication procedure was repeated. Following another incubation on ice for at least 1 h, lysates were clarified by centrifugation (16,100×g, 5 min, 22° C.) and the supernatant was used for enzyme assays.

Enzyme activity of cell-free extracts was determined by measuring the formation of nitrite from 0.2 mM nitroglycerin and 0.2 mM NADPH in 50 mM potassium phosphate pH 7.2 at room temperature. Assays were terminated at various time points by addition of 0.2 mM phenazine methosulfate and 0.5 mM ferricyanide. Nitrite concentration was determined by mixing 100 µL of sample with 900 µL of 10 mg/mL nitrite reagent (Sigma, cat#37410) and measuring absorbance at 530 nm after 10 minutes. One unit of activity was defined as the amount of enzyme required to release 1 µmol of nitrite per min from nitroglycerin at room temperature (~22° C.) and was expressed per gram of protein. Protein concentrations were determined using Bradford reagent (Bio-Rad) according to manufacturer's instructions.

Figure 12:
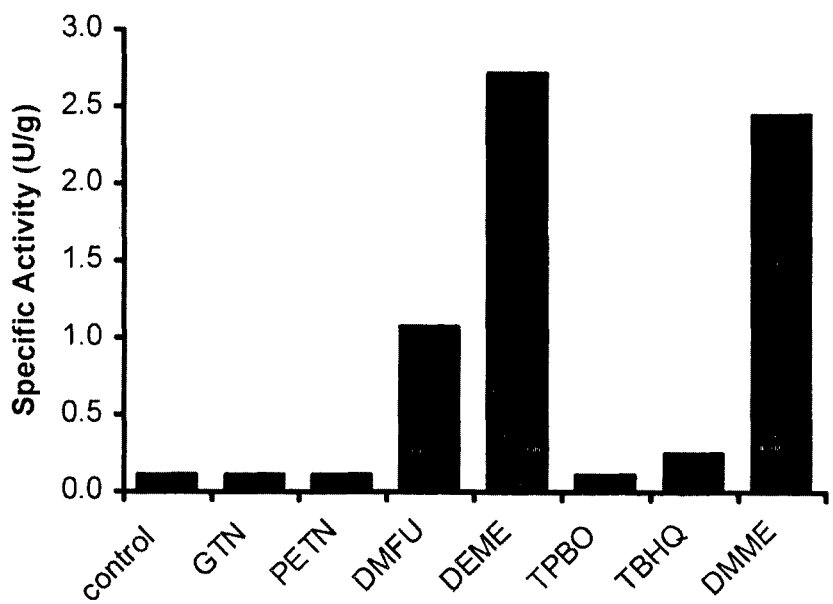

The results are shown in FIG. 12 and the table below, which clearly shows an increase in nitroglycerin-degrading activity when G. moniliformis CD611 is exposed to DMFU, DEME, TBHQ and DMME with increases of 11-, 27-, 2.5- and 25-fold respectively relative to the control. Growth was inhibited in the presence of TNT, NEM, MD and 3HC, therefore insufficient biomass was available to measure enzyme activity for these samples. The explosive compounds GTN or PETN did not illicit any significant response. Enzyme induction in this fungal strain is further evidence that this induction mechanism is not confined solely to bacteria.

| Chemical | U/g | Fold-Induction |
| --- | --- | --- |
| control | <0.10 | 1.0 |
| GTN | <0.10 | 1.0 |
| PETN | <0.10 | 1.0 |
| TNT | — | — |
| NEM | — | — |
| MD | — | — |
| DMFU | 1.1 | 11 |
| DEME | 2.7 | 27 |
| 3HC | — | — |
| TPBO | <0.10 | 1.0 |
| TBHQ | 0.25 | 2.5 |
| DMME | 2.5 | 25 |

EXAMPLE 7

Induction of nitroglycerin-Degrading Activity in a Mixed Soil Culture

A mixed soil culture was generated by inoculating 10 g of soil into 100 mL of Luria Broth. The soil was obtained locally (Bundoora, VIC, Australia) and to the authors knowledge had not previously been exposed to any contamination. The soil slurry was incubated overnight at 30° C. with shaking at 200 rpm and was then inoculated 10% v/v (1 mL into 9 mL) into fresh Luria Broth containing various test compounds and incubated for a further 24 h. The inducer compounds tested were 0.5 mM glycerol trinitrate (GTN), 0.5 mM pentaerythritol tetranitrate (PETN), 0.5 mM trinitrotoluene (TNT), 0.5 mM N-ethylmaleimide (NEM), 0.25 mM menadione (MD), 1 mM dimethyl fumarate (DMFU), 4 mM diethyl maleate (DEME), 1 mM 3-hydroxycoumarin (3HC), 1 mM trans-4-phenyl-3-buten-2-one (TPBO), 1 mM tert-butyl-hydroquinone (TBHQ) and 1 mM dimethyl maleate (DMME). Controls without test, compound were included and the media also contained up to 1% v/v ethanol from the inducer stock solutions, which did not affect growth or enzyme expression (or acetone in the case of PETN and TNT). Cells were harvested by centrifugation (3220×g, 15 min, 4° C.), washed in 50 mM potassium phosphate pH 7.2 and the pellets were stored at −20° C. Pellets were resuspended in 1.5 mL of lysis buffer (50 mM Tris pH 8, 100 mM NaCl, 0.5% Triton X-100) and sonicated for 3×15 s pulses at 35% power with 30 s rest between pulses using a Branson Digital Sonifier. Following incubation on ice for at least 1 h, lysates were clarified by centrifugation (16,100×g, 5 min, 22° C.) and the supernatant was used for enzyme assays.

Enzyme activity of cell-free extracts was determined by measuring the formation of nitrite from 0.2 mM nitroglycerin and 0.2 mM NADPH in 50 mM potassium phosphate pH 7.2 at room temperature. Assays were terminated at various time points by addition of 0.2 mM phenazine methosulfate and 0.5 mM ferricyanide. Nitrite concentration was determined by mixing 100 µL of sample with 900 µL of 10 mg/mL nitrite reagent (Sigma, cat#37410) and measuring absorbance at 530 nm after 10 minutes. One unit of activity was defined as the amount of enzyme required to release 1 µmol of nitrite per min from nitroglycerin at room temperature (~22° C.) and was expressed per gram of protein. Protein concentrations were determined using Bradford reagent (Bio-Rad) according to manufacturer's instructions.

Figure 13:
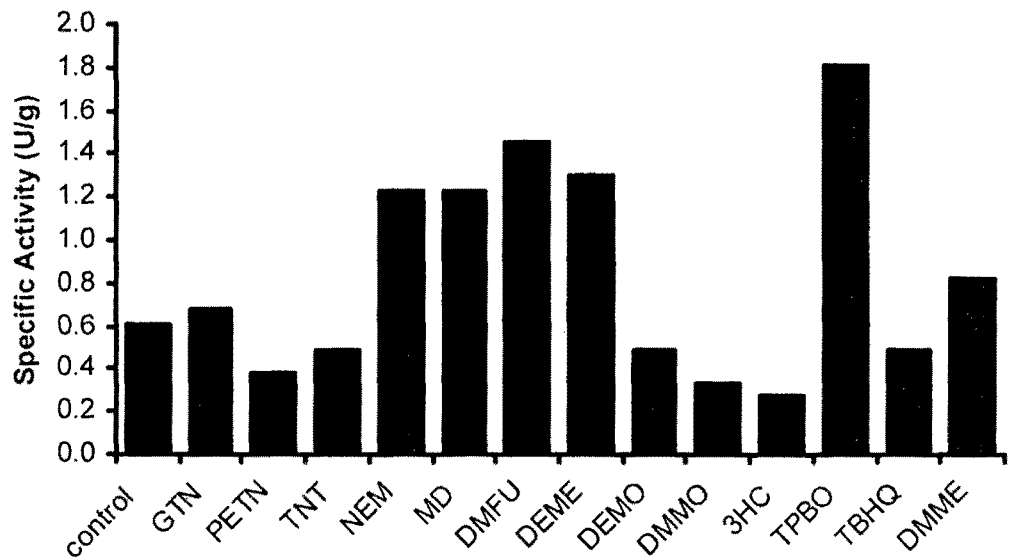

The results are shown in FIG. 13 and the table below, which clearly shows an increase in nitroglycerin-degrading activity when soil microbes are exposed to NEM, MD, DMFU, DEME and TPBO with increases of 2.0-, 2.0-, 2.4-, 2.1 and 3.0-fold respectively relative to the control. This is an important result as it demonstrates a measurable increase in explosive-degrading activity of naive soil microbes under non-selective conditions and it also indicates that the inducer compounds retain their activity in the presence of a 1% w/v soil slurry.

| Chemical | U/g | Fold-Induction |
| --- | --- | --- |
| control | 0.61 | 1.0 |
| GTN | 0.68 | 1.1 |
| PETN | 0.38 | 0.63 |
| TNT | 0.49 | 0.81 |
| NEM | 1.2 | 2.0 |
| MD | 1.2 | 2.0 |
| DMFU | 1.5 | 2.4 |
| DEME | 1.3 | 2.1 |
| DEMO | 0.49 | 0.81 |
| DMMO | 0.33 | 0.55 |
| 3HC | 0.27 | 0.44 |
| TPBO | 1.8 | 3.0 |
| TBHQ | 0.49 | 0.8 |
| DMME | 0.82 | 1.4 |

EXAMPLE 8

Induction of nitroglycerin-Degrading Activity in Escherichia coli DH5α with Different Dose Rates of dimethyl fumarate and diethyl maleate An overnight culture of Escherichia coli DH5α grown at 30° C. with shaking at 200 rpm in Luria Broth was inoculated 10% v/v (1 mL into 9 mL) into the same medium containing various concentrations of dimethyl fumarate (DMFU) or diethyl maleate (DEME) and incubated for a further 24 h. The concentrations used were 0.01, 0.05, 0.1, 0.5, 0.75 and 1 mM for DMFU and 0.1, 0.25, 0.5, 0.75, 1, 2 and 4 mM for DEME. Controls without test compound were included and the media also contained up to 1% v/v ethanol from the inducer stock solutions, which did not affect growth or enzyme expression. Cells were harvested by centrifugation (3220×g, 15 min, 4° C.), washed in 50 mM potassium phosphate pH 7.2 and the pellets were stored at −20° C. Pellets were resuspended in 1.5 mL of lysis buffer (50 mM Tris pH 8, 100 mM NaCl, 0.5% Triton X-100) and sonicated for 3×15 s pulses at 35% power with 30 s rest between pulses using a Branson Digital Sonifier. Following incubation on ice for at least 1 h, lysates were clarified by centrifugation (16,100×g, 5 min, 22° C.) and the supernatant was used for enzyme assays.

Enzyme activity of cell-free extracts was determined by measuring the formation of nitrite from 0.2 mM nitroglycerin and 0.2 mM NADPH in 50 mM potassium phosphate pH 7.2 at room temperature. Assays were terminated at various time points by addition of 0.2 mM phenazine methosulfate and 0.5 mM ferricyanide. Nitrite concentration was determined by mixing 100 µL of sample with 900 µL of 10 mg/mL nitrite reagent (Sigma, cat#37410) and measuring absorbance at 530 nm after 10 minutes. One unit of activity was defined as the amount of enzyme required to release 1 µmol of nitrite per min from nitroglycerin at room temperature (~22° C.) and was expressed per gram of protein. Protein concentrations were determined using Bradford reagent (Bio-Rad) according to manufacturer's instructions.

Figure 14:
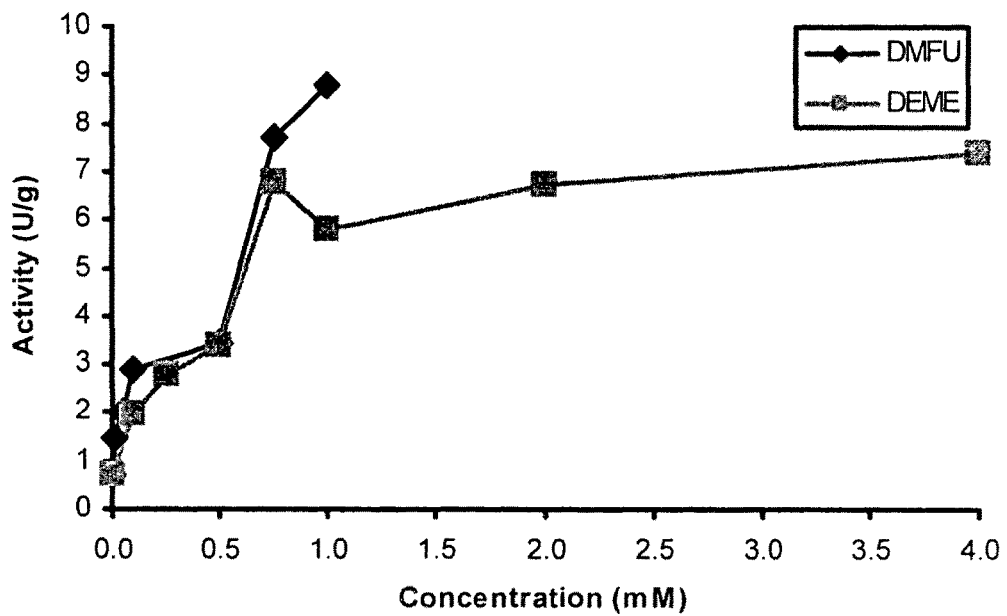

The results are shown in FIG. 14, which clearly shows an increase in nitroglycerin-degrading activity with increasing concentrations of DMFU and DEME. At the highest concentrations tested, enzyme activity increased 13-fold for DMFU and 11-fold for DEME relative to the control. However, even as low as 0.01 mM DMFU was sufficient to increase enzyme activity by 2.2-fold relative to the control and 0.1 mM DEME resulted in a 2.8-fold increase.

EXAMPLE 9

Induction of nitroglycerin-Degrading Activity in Escherichia coli DH5α with Different Dose Rates of 3-hydroxycoumarin, tert-butyl-hydroquinone and dimethyl maleate An overnight culture of Escherichia coli DH5α grown at 30° C. with shaking at 200 rpm in Luria Broth was inoculated 10% v/v (1 mL into 9 mL) into the same medium containing various concentrations of 3-hydroxycoumarin (3HC), tert-butyl-hydroquinone (TBHQ) and dimethyl maleate (DMME) and incubated for a further 24 h. The concentrations used were 0.25, 0.5, 2 and 4 mM for 3HC, 0.5, 1, 2 and 4 mM for TBHQ and 0.5, 1, 2 and 4 mM for DMME. Controls without test compound were included and the media also contained up to 1% v/v ethanol from the inducer stock solutions, which did not affect growth or enzyme expression. Cells were harvested by centrifugation (3220×g, 15 min, 4° C.), washed in 50 mM potassium phosphate pH 7.2 and the pellets were stored at −20° C. Pellets were resuspended in 1.5 mL of lysis buffer (50 mM Tris pH 8, 100 mM NaCl, 0.5% Triton X-100) and sonicated for 3×15 s pulses at 35% power with 30 s rest between pulses using a Branson Digital Sonifier. Following incubation on ice for at least 1 h, lysates were clarified by centrifugation (16,100×g, 5 min, 22° C.) and the supernatant was used for enzyme assays.

Enzyme activity of cell-free extracts was determined by measuring the formation of nitrite from 0.2 mM nitroglycerin and 0.2 mM NADPH in 50 mM potassium phosphate pH 7.2 at room temperature. Assays were terminated at various time points by addition of 0.2 mM phenazine methosulfate and 0.5 mM ferricyanide. Nitrite concentration was determined by mixing 100 µL, of sample with 900 µL of 10 mg/mL nitrite reagent (Sigma, cat#37410) and measuring absorbance at 530 nm after 10 minutes. One unit of activity was defined as the amount of enzyme required to release 1 µmol of nitrite per min from nitroglycerin at room temperature (~22° C.) and was expressed per gram of protein. Protein concentrations were determined using Bradford reagent (Bio-Rad) according to manufacturer's instructions.

Figure 15:
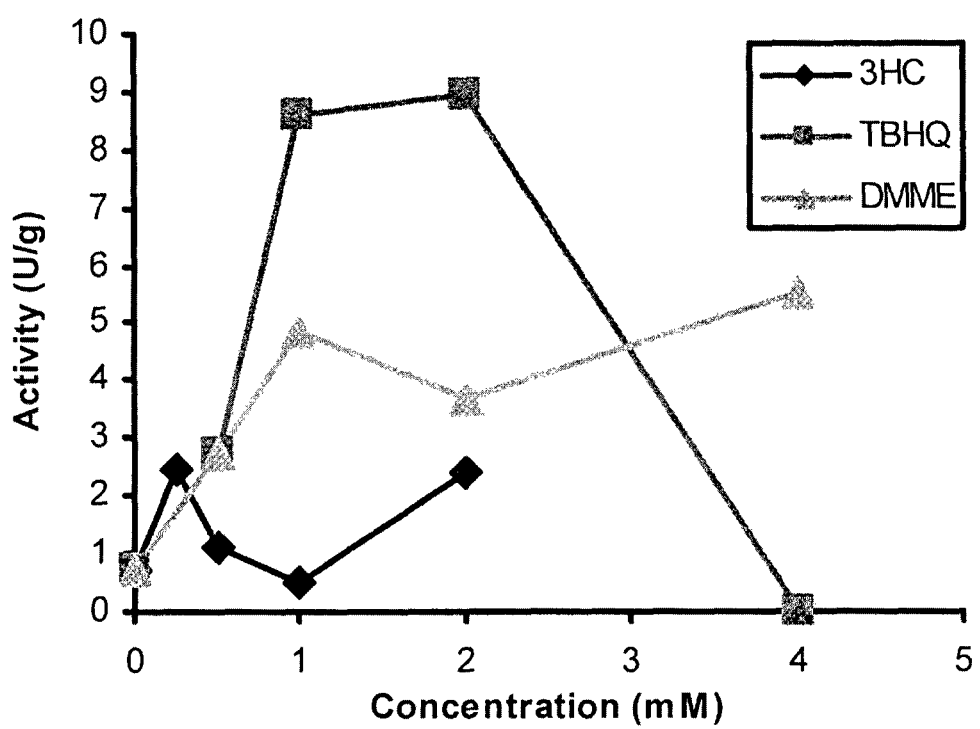

The results are shown in FIG. 15, which clearly shows an increase in nitroglycerin-degrading activity with increasing concentrations of DMME, but 3HC and TBHQ resulted in a rise and fall in activity as concentrations increased. Both these inducers were mildly toxic to E. coli DH5α with higher concentrations resulting in reduced protein yields, which may explain the lower expression levels. For 3HC, activity did increase from 1 to 2 mM possibly due to the increase in enzyme expression levels being greater than the reduction in protein yield. However, TBHQ peaked at 2 mM and then dropped to undetectable levels at 4 mM. These results highlight the importance of maintaining a balance between toxicity and inducer potency in order to achieve a good level of enzyme induction without adversely affecting the microbial population. It also indicates that a gradual sustained release of inducer compound may be a more appropriate means of presenting the inducer to prevent high local concentrations from occurring.

EXAMPLE 10

Induction of Nitroglycerin-Degrading Activity in Escherichia coli DH5α with Different Dose Rates of trans-4-phenyl-buten-2-one An overnight culture of Escherichia coli DH5α grown at 30° C. with shaking at 200 rpm in Luria Broth was inoculated 10% v/v (1 mL into 9 mL) into the same medium containing 0.5, 2 or 4 mM trans-4-phenyl-3-buten-2-one (TPBO) and incubated for a further 24 h. Controls without test compound were included and the media also contained up to 1% v/v ethanol from the inducer stock solutions, which did not affect growth or enzyme expression. Cells were harvested by centrifugation (3220×g, 15 min, 4° C.), washed in 50 mM potassium phosphate pH 7.2 and the pellets were stored at −20° C. Pellets were resuspended in 1.5 mL of lysis buffer (50 mM Tris pH 8, 100 mM NaCl, 0.5% Triton X-100) and sonicated for 3×15 s pulses at 35% power with 30 s rest between pulses using a Branson Digital Sonifier. Following incubation on ice for at least 1 h, lysates were clarified by centrifugation (16,100×g, 5 min, 22° C.) and the supernatant was used for enzyme assays.

Enzyme activity of cell-free extracts was determined by measuring the formation of nitrite from 0.2 mM nitroglycerin and 0.2 mM NADPH in 50 mM potassium phosphate pH 7.2 at room temperature. Assays were terminated at various time points by addition of 0.2 mM phenazine methosulfate and 0.5 mM ferricyanide. Nitrite concentration was determined by mixing 100 µL of sample with 900 µL of 10 mg/mL nitrite reagent (Sigma, cat#37410) and measuring absorbance at 530 nm after 10 minutes. One unit of activity was defined as the amount of enzyme required to release 1 µmol of nitrite per min from nitroglycerin at room temperature (~22° C.) and was expressed per gram of protein. Protein concentrations were determined using Bradford reagent (Bio-Rad) according to manufacturer's instructions.

Figure 16:
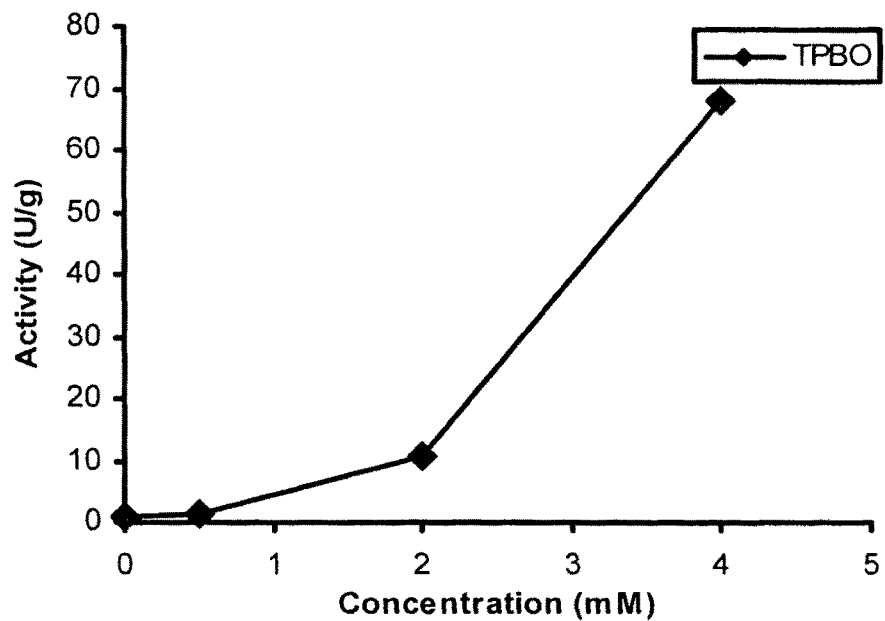

The results are shown in FIG. 16, which clearly shows an increase in nitroglycerin-degrading activity with increasing concentrations of TPBO. This inducer was very potent with a 97-fold increase in enzyme activity observed at a dose rate of 4 mM, however, this concentration also resulted in an 87% decrease in the protein yield due to growth inhibition. These results highlight the importance of maintaining a balance between toxicity and inducer potency in order to achieve a good level of enzyme induction without adversely affecting the microbial population.

EXAMPLE 11

Induction of Pentolite Degradation in Soil Microcosms by Inducer Mixtures Containing diethyl maleate, dimethyl fumarate or tert-butyl hydroquinone Microcosms were prepared in 40 mL glass vials by inoculating 1 g of sieved soil into 5 mL of Reconstituted Natural Water (RNW: 1 mM KHCO3, 0.5 mM CaCl2, 0.206 mM MgSO4, 8.95 µM FeSO4, 0.25 mM HCl, pH ~7.8) containing 100 mg/L Pentolite and 5 g/L of various inducer mixtures. The soil was obtained locally (Bundoora. VIC, Australia) and to the authors knowledge had not previously been exposed to any contamination. Inducer mixtures contained (by weight) 94% sucrose, 5% monosodium phosphate and 1% of either diethyl maleate (DEME), dimethyl fumarate (DMFU) or tert-butyl hydroquinone (TBHQ). Control microcosms without inducer mixture were included and were either non-sterile or sterile (soil autoclaved 121° C. for 100 min and RNW filter sterilised through 0.2 µm filter). Reactions were commenced by the addition of 50 µL of 1% w/v Pentolite solution (50/50 trinitrotoluene/pentaerythritol tetranitrate) in acetone for a final concentration of 100 mg/L. Vials were incubated in the dark at room temperature (~22° C.) and after 24 h or 7 days, 15 mL of acetonitrile was added to solubilise the TNT and PETN. Samples were analysed using HPLC-UV with a limit of detection of 0.1 mg/L. Prior to acetonitrile addition, 10 µL samples from the sterile controls were inoculated into 5 mL of 2YTG medium and left at room temperature for 7 days to confirm sterility of the samples. No growth was observed in these sterility tests.

Figure 17:
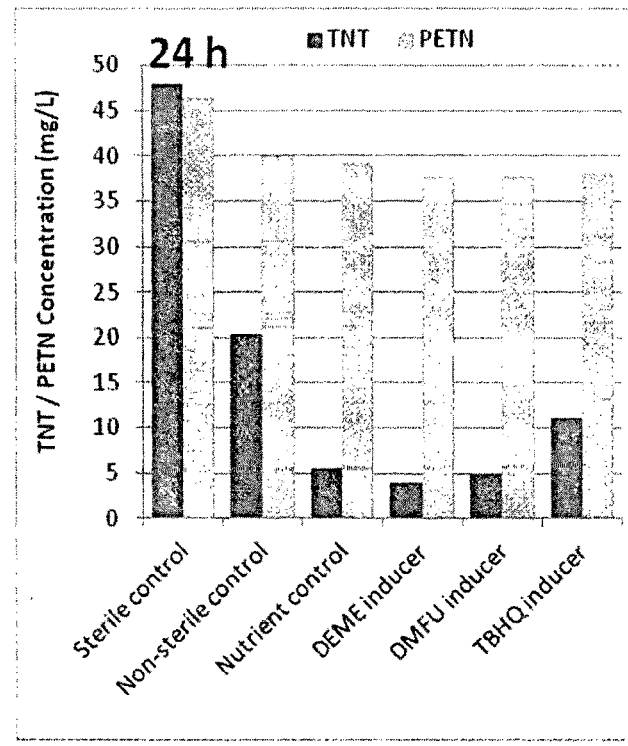
Figure 18:
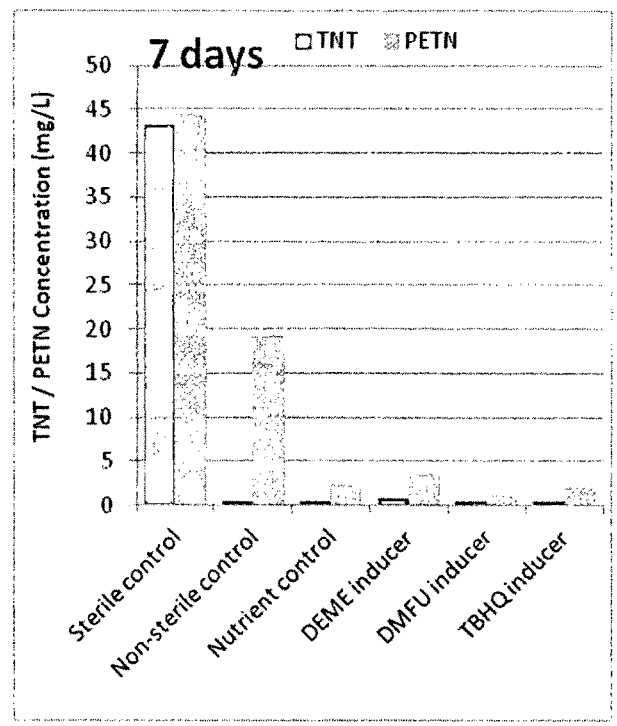

The results are shown in FIGS. 17 and 18, which clearly show an increased rate of Pentolite degradation in the presence of inducer mixtures. TNT degradation was rapid with 92% TNT breakdown observed for the DEME treatment over the first 24 h at a removal rate of 1.83 mg/L/h. This corresponds to a 59% rate increase compared with the non-sterile control removal rate of 1.15 mg/L/h. Removal rates were increased 57% for DMFU and 33% for TBHQ inducer mixtures. Over 98% TNT degradation was observed for all samples after 7 days except for the sterile control.

PETN degradation was slower with 19% PETN breakdown observed for DEME and DMFU treatments over the first 24 h at a removal rate of 0.367 mg/L/h. This corresponds to a 38% rate increase compared with the non-sterile control removal rate of 0.267 mg/L/h. Removal rates were increased 31% for TBHQ. After 7 days, >92% PETN degradation had occurred for all inducer treatments compared with 57% for the non-sterile control. Removal rates had dropped slightly after 7 days with an average rate of 0.257 mg/L/h observed for the DMFU treatment, which was 71% higher than that for the non-sterile control at 0.150 mg/L/h.

EXAMPLE 12

Induction of Pentolite Degradation in Soil Microcosms by Different Concentrations of Inducer Mixtures Containing Dimethyl Fumarate Microcosms were prepared in 40 mL glass vials by inoculating 1 g of sieved soil into 5 mL of Reconstituted Natural Water (RNW: 1 mM KHCO3, 0.5 mM CaCl2, 0.206 mM MgSO4, 8.95 µM FeSO4, 0.25 mM HCl, pH ~7.8) containing 2000 mg/L Pentolite and 0.5, 2 or 5 g/L of inducer mixture containing dimethyl fumarate (DMFU). The soil was obtained locally (Bundoora, VIC, Australia) and to the authors knowledge had not previously been exposed to any contamination. Inducer mixture contained (by weight) 94% sucrose, 5% monosodium phosphate and 1% DMFU. Control microcosms without inducer mixture were included and were either non-sterile or sterile (soil autoclaved 121° C. for 100 min and RNW filter sterilised through 0.2 µm filter). Pentolite was added to empty vials as 1 mL of 1% w/v Pentolite solution (50/50 trinitrotoluene/pentaerythritol tetranitrate) in acetone, which was then evaporated overnight leaving 10 mg of solid Pentolite. Five millilitres of appropriate solution was added with mixing by vortexing giving a final Pentolite concentration of 2000 mg/L (mostly insoluble). Reactions were commenced by addition of 1 g of soil resulting in a Pentolite/soil ratio of 10,000 mg/kg. Vials were incubated in the dark at room temperature (~22° C.) and after 24 h, 7 days or 28 days, 15 mL of acetonitrile was added to solubilise the TNT and PETN. Samples were analysed using HPLC-UV with a limit of detection of 0.1 mg/L. Prior to acetonitrile addition, 10 µL samples from the sterile controls were inoculated into 5 mL of 2YTG medium and left at room temperature for 7 days to confirm sterility of the samples. No growth was observed in these sterility tests.

Figure 19:
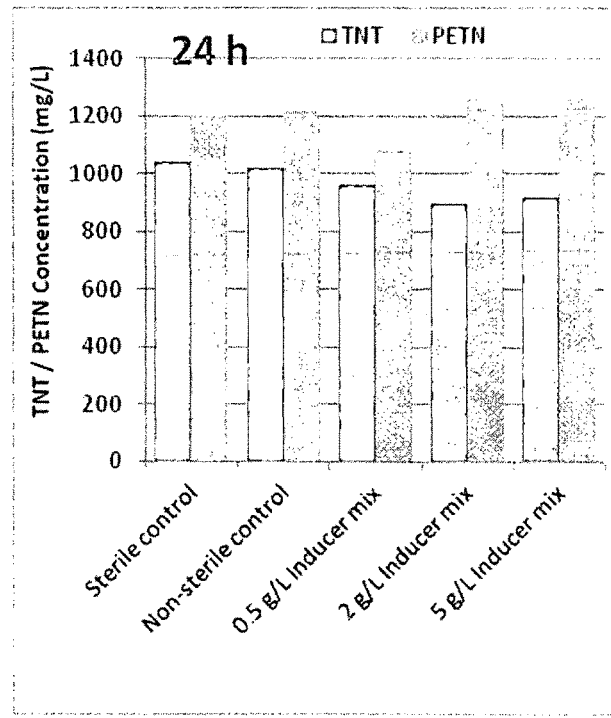
Figure 20:
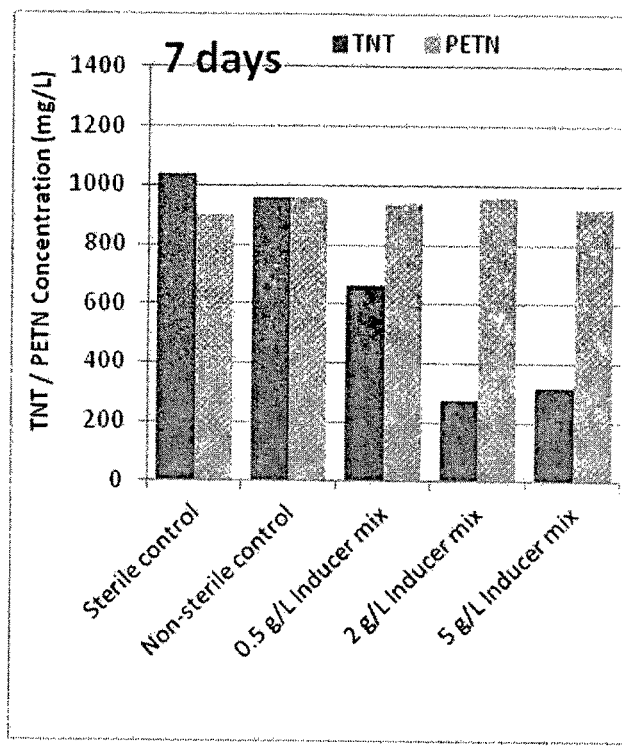
Figure 21:
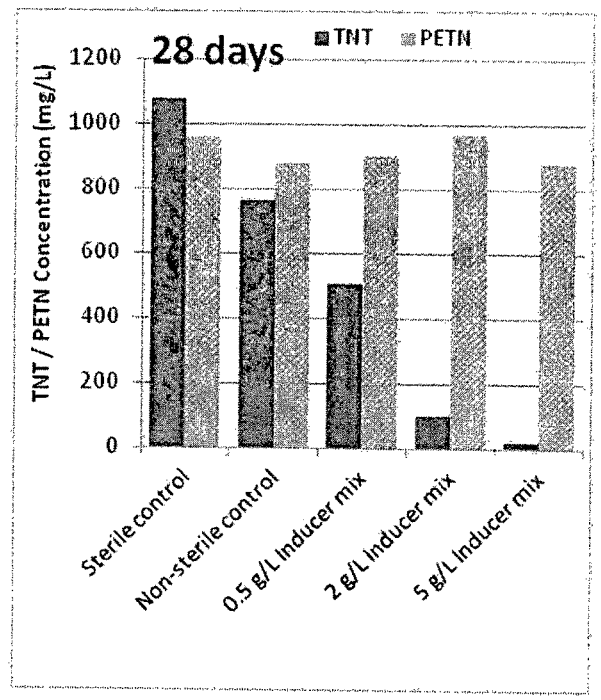

The results are shown in FIGS. 19, 20 and 21, which clearly show an increased rate of Pentolite degradation in the presence of inducer mixtures. TNT degradation was rapid with 74% TNT breakdown observed for the 2 g/L inducer mix treatment over 7 days at a removal rate of 4.55 mg/L/h. This corresponds to a 9.6-fold rate increase compared with the non-sterile control removal rate of 0.467 mg/L/h and only 8% degradation. Up to 98% TNT degradation was observed after 28 days with 5 g/L inducer compared with 27% for the non-sterile control.

PETN concentration for all samples, including the sterile-control, had dropped 17-25% at a rate of 1.2-1.8 mg/L/h over 7 days possibly due to strong binding of the PETN to soil. After 28 days, concentrations were similar for all samples (880-1000 mg/L) indicating that PETN degradation was not occurring under these conditions. This may be due to the high initial concentrations of TNT that would be preferentially used by microbes as a nitrogen source, as it is more readily soluble and more easily biodegraded. Longer incubation times may be necessary before significant PETN degradation could be observed.

The claims defining the invention are as follows:
1. A method, comprising:
placing an explosive cartridge containing an explosive composition and a Michael acceptor into an environment of a blasting operation, the explosive cartridge being detonable when placed into the environment, the environment containing a microorganism indigenous to the environment, the microorganism capable of producing an enzyme that degrades the explosive composition, the Michael acceptor promoting production of the enzyme by the microorganism, placing the explosive cartridge into the environment exposing the Michael acceptor and the explosive composition to the microorganism; and allowing the enzyme produced by the microorganism to degrade the explosive composition thereby deactivating the explosive composition and rendering the explosive cartridge non-detonable.

2. The method of claim 1, wherein the microorganism is selected from the group consisting of *Pseudomonas* spp., *Escherichia coli, Morganella morganii, Rhodococcus* spp., *Comamanos* spp., *Agrobacterium radiobacter, Enterobacter cloacae, Agrobacterium tumifaciens, Klebsiella pneumonia, and Gibberella moniliformis.*

3. The method of claim 1, wherein the enzyme that degrades the explosive composition is selected from the group consisting of Old Yellow Enzyme (OYE), a glycerol trinitrate (GTN) reductase, a nitroreductase, and an N-ethyl maleimide (NEM) reductase.

4. The method of claim 1, wherein the Michael acceptor is selected from menadione (vitamin K precursor), dimethyl maleate, 3-hydroxycoumarin, o-coumaric acid, trans-4-phenyl-3-buten-2-one, N-ethylmaleimide, dimethyl fumarate, diethyl maleate, and tert-butyl-hydroquinone.

5. The method of claim 1, wherein:

the environment contains water; and the microorganism is transported into the explosive cartridge by the water present in the environment.

6. The method of claim 5, wherein the explosive cartridge comprises at least one of an inlet or a water-degradable pathway to allow environmental water to flow into the cartridge and directly into contact with the explosive composition and the chemical inducing agent provided in the explosive composition.

7. The method of claim 5, wherein the explosive composition comprises channels to allow the water present in the environment to travel through it and into contact with the chemical inducing agent.

8. The method of claim 5, wherein the explosive cartridge comprises a water-permeable or water-degradable outer shell surrounding the explosive composition.

9. The method of claim 1, wherein the Michael acceptor is included in or on one or more outer walls of the explosive cartridge.

10. The method of claim 9, wherein the one or more outer walls are direct contact with the explosive composition and are water-permeable, water-degradable or water-soluble.

11. The method of claim 1, wherein:

the explosive composition is provided in a first chamber of the explosive cartridge;

the environment contains water; and the Michael acceptor is provided in a second chamber of the explosive cartridge separate from the first chamber such that the water present in the environment enters the second chamber thereby bringing the microorganism into contact with the Michael acceptor.

12. The method of claim 1, wherein:

the explosive composition comprises a nutrient source to support growth of the microorganism and expression of the enzyme; and the nutrient source is different from the Michael acceptor.

13. The method of claim 1, wherein the microorganism is a denitrifying bacteria.

14. The method of claim 1, wherein the enzyme produced by the microorganism is a glycerol trinitrate (GTN) reductase.

15. The method of claim 1, further comprising placing the explosive cartridge into the environment via a borehole, the explosive cartridge being detonable when placed into the environment, the microorganism being indigenous to and present within soil associated with the environment.

16. The method of claim 1, wherein the microorganism is selected from the group consisting of *Pseudomonas* spp., *Escherichia coli, Morganella morganii, Comamanos* spp., *Enterobacter cloacae, Klebsiella pneumonia*, and *Gibberella moniliformis.*

17. The method of claim 1, wherein the microorganism is *Escherichia coli*, and the Michael acceptor is diethyl maleate (DEME).

18. The method of claim 1 wherein the microorganism is *Klebsiella pneumonia* and the Michael acceptor is dimethyl fumarate (DMFU).

19. The method of claim 1, wherein the microorganism is *Pseudomonas* spp. and the Michael acceptor is menadione (MD).

* * * * *